(12) United States Patent
Iji et al.

(10) Patent No.: US 8,507,095 B2
(45) Date of Patent: Aug. 13, 2013

(54) METAL OXIDE-BASED FINE PARTICLE AND METHOD FOR MANUFACTURING THE SAME, AND RESIN COMPOSITION

(75) Inventors: Masatoshi Iji, Minato-ku (JP); Naoki Morishita, Minato-ku (JP); Hiroyuki Kai, Minato-ku (JP)

(73) Assignee: NEC Corporation, Tokyo (JP)

( * ) Notice: Subject to any disclaimer, the term of this patent is extended or adjusted under 35 U.S.C. 154(b) by 330 days.

(21) Appl. No.: 12/991,937

(22) PCT Filed: May 15, 2009

(86) PCT No.: PCT/JP2009/059050
§ 371 (c)(1),
(2), (4) Date: Nov. 10, 2010

(87) PCT Pub. No.: WO2009/139463
PCT Pub. Date: Nov. 19, 2009

(65) Prior Publication Data
US 2011/0061567 A1    Mar. 17, 2011

(30) Foreign Application Priority Data

May 16, 2008  (JP) .................... 2008-129585
Feb. 6, 2009   (JP) .................... 2009-026361

(51) Int. Cl.
*B32B 5/16* (2006.01)

(52) U.S. Cl.
USPC ........... 428/403; 428/404; 428/405; 428/406; 428/407; 427/212

(58) Field of Classification Search
USPC .................. 428/403–407; 427/212
See application file for complete search history.

(56) References Cited

U.S. PATENT DOCUMENTS

| | | | | |
|---|---|---|---|---|
| 6,071,987 A | * | 6/2000 | Matsumoto et al. | .......... 523/209 |
| 2005/0261380 A1 | * | 11/2005 | Suzuki et al. | .................. 516/77 |
| 2007/0298256 A1 | | 12/2007 | Fukui et al. | |

FOREIGN PATENT DOCUMENTS

| | | | |
|---|---|---|---|
| JP | 62-236821 A | | 10/1987 |
| JP | 03-281536 A | | 12/1991 |
| JP | 06-136321 A | | 5/1994 |
| JP | 07-178335 A | | 7/1995 |
| JP | 10-036675 A | | 2/1998 |
| JP | 10-36675 A | * | 2/1998 |
| JP | 10-251407 A | | 9/1998 |
| JP | 11-148009 A | * | 6/1999 |
| JP | 11-148009 A | | 6/1999 |
| JP | 2001-064439 A | | 3/2001 |
| JP | 2002-121536 A | | 4/2002 |
| JP | 2002-327030 A | | 11/2002 |
| JP | 2004-269773 A | | 9/2004 |
| JP | 2004-277476 A | | 10/2004 |
| JP | 2004-277476 A | * | 10/2004 |
| JP | 2006-022207 A | | 1/2006 |
| JP | 2006-183021 A | | 7/2006 |
| JP | 2007-224312 A | * | 9/2007 |
| JP | 2007224312 A | | 9/2007 |
| JP | 2007-308867 A | | 11/2007 |
| JP | 2008-081728 A | | 4/2008 |
| JP | 2008-120870 A | | 5/2008 |
| WO | 2006/059719 A1 | | 6/2006 |
| WO | 2006/107226 A1 | | 10/2006 |
| WO | 2007/061847 A1 | | 5/2007 |

OTHER PUBLICATIONS

Chinese Office Action dated May 3, 2012 issued by the State Intellectual Property Office of the People's Republic of China in counterpart Chinese Application No. 200980117763.1.

* cited by examiner

*Primary Examiner* — Leszek Kiliman
(74) *Attorney, Agent, or Firm* — Sughrue Mion, PLLC

(57) ABSTRACT

A metal oxide-based fine particle includes a metal oxide-based core region; an intermediate region formed on the outer periphery of the core region, the intermediate region having an alkoxyorganosiloxane condensate structure; and a surface region including an organic molecular chain or an organic silicon molecular chain or a reactive functional group.

18 Claims, No Drawings

METAL OXIDE-BASED FINE PARTICLE AND METHOD FOR MANUFACTURING THE SAME, AND RESIN COMPOSITION

TECHNICAL FIELD

The present invention relates to a metal oxide-based fine particle and a method for manufacturing the same, and a resin composition.

BACKGROUND ART

Plastics are used in various industrial fields, and particularly in durable goods, such as electronic equipment and automobiles, an improvement in strength is required.

For related art for improving the strength of plastics, metal oxides (silica, alumina, titania, and the like) in the form of fine particles are added as fillers. In recent years, attention has been paid to the high reinforcement effect of the addition of silica ultrafine particles having a diameter of 1 micron or less, particularly nanosize.

However, silica fine particles aggregate easily because of the hydroxyl groups on the surface, and therefore, the dispersibility in a plastic is low. In addition, the adhesion at the plastic/fine particle interface may be insufficient, depending on the type of a plastic, and frequently, a sufficient improvement effect is not obtained.

Accordingly, the dispersibility of silica fine particles in a plastic, and the adhesion at the plastic/fine particle interface are improved by treating the surface of the silica fine particles with reactive organic compounds, for example, organometallic compounds, such as organic silicon compounds, organic aluminum compounds, and organic titanium compounds, and various carboxylic acids. For example, Patent Document 1 (JP2004-269773A) describes that by sequentially surface-treating an oxide compound, such as silica, using a modifier including a hydrophobic group, and a modifier including a polar group, and adding the oxide compound to a thermoplastic resin, a resin composition in which the oxide compound is uniformly dispersed and firmly bonded to a functional group of the thermoplastic resin is obtained. In addition, Patent Document 2 (JP62-236821A) describes an epoxy resin composition for sealing a semiconductor including a mixture of an epoxy resin, a curing agent, and an inorganic filler in which the surface of an inorganic substance, such as silica, is sequentially coated with a silicone rubber layer and a layer reactive with the resin.

For another surface treatment technique, higher functionality is studied, for example, the stress in the surface layer of silica fine particles is relaxed by providing a specific organic compound layer, for example, a polysiloxane layer, on the surface of the silica fine particles. As an example of this, Patent Document 3 (JP2002-327030A) describes a core-shell type fine particle including a silica fine particle as a core, and a shell layer including a polyorganosiloxane and a polymer of a hydrophobic polymerizable monomer provided on the surface of the silica fine particle via a covalent bond.

On the other hand, in recent years, the so-called sol-gel nanocomposites have been studied in which an alkoxysilane compound is previously mixed in a plastic, and then, the alkoxy groups are condensed to form nanosized silica fine particles or fine particles having a structure similar to that of the nanosized silica fine particles (hereinafter, these are collectively referred to as "silica-based fine particles") in the plastic. This method is effective for higher dispersion of silica-based fine particles in a plastic, and as a result, a high reinforcement effect, particularly an improvement in rigidity (elastic niodulus, Young's modulus), can be promoted. As an example of this, for example, Patent Document 4 (JP6-136321A) describes that a polyurethane-silica hybrid is manufactured by dissolving polyurethane, hydrolyzable alkoxysilane (or a partial condensate thereof), and a catalyst, as required, in a lower alcohol, applying the obtained alcohol sol solution to a substrate, and drying the alcohol sol solution. In addition, Patent Document 5 (JP2006-183021A) describes that a polyurethane-polysilicic acid composite is obtained by reacting water-dispersible polyurethane having a hydrophilic group, silicate, and an acid, or reacting this water-dispersible polyurethane and alkylsilicic acid under a neutral or alkaline condition to simultaneously precipitate polyurethane and polysilicic acid.

DISCLOSURE OF THE INVENTION

Surface-modified fine particles obtained by surface treatment using various organic compounds, as described above, are effective in improving function when the fine particles are combined with a plastic. But, a surface treatment step, such as the spraying of a surface treatment agent on fine particles, or the immersion of fine particles in a treatment agent solution, is necessary. The treatment itself requires time and effort, and the manufacturing process is cumbersome. In the surface treatment step, fine particles aggregate easily, particularly, ultrafine particles with a diameter of 1 micron or less aggregate easily. Therefore, it is difficult to perform the surface treatment of the fine particles, while preventing aggregation. As a result, the problems of an insufficient treatment effect and increased aggregates in a product occur. In addition, when a plurality of layers having different functions are formed on the fine particle surface, a more complicated step is required, and enormous time and effort are required. Further, the surface treatment agents react easily with each other, and therefore, the treatment efficiency decreases, and the recovery and reuse of the remaining treatment agents are difficult. Therefore, a problem is that the productivity of metal oxide fine particles with higher functionality achieved by surface treatment is extremely low.

On the other hand, the sol-gel nanocomposite techniques as described above are effective for higher dispersion of fine particles in a plastic. But, although such nanocomposite techniques are effective in improving the rigidity of a plastic, they are insufficient for elongation (at break or at maximum stress). In other words, the approach to higher functionality of the surface of nanosized ultrafine particles is insufficient, and it is an important problem to improve elongation together with maximum stress at break, that is, to improve toughness.

It is an object of the present invention to provide a metal oxide-based fine particle effective in improving the strength of a plastic, and a method for manufacturing the same, and a resin composition with improved strength, which solve the above-described problems.

According to aspects of the present invention, it is possible to provide the following metal oxide-based fine particle and method for manufacturing the same, and resin composition.

(1) A metal oxide-based fine particle including:

a metal oxide-based core region;

an intermediate region including an alkoxyorganosiloxane condensate structure, the intermediate region being formed on the outer periphery of the core region; and a surface region including an organic molecular chain or an organic silicon molecular chain or a reactive functional group.

(2) The metal oxide-based fine particle according to the above item 1, wherein the organic molecular chain or the organic silicon molecular chain or the reactive functional group of the surface region is bonded to a silicon atom of the condensate structure of the intermediate region via a linking group, and a silicon atom of the condensate structure of the intermediate region and a metal atom of the metal oxide-based core region are bonded via a linking group.

(3) The metal oxide-based fine particle according to the above item 1 or item 2, wherein the metal oxide-based fine particle is a fine particle formed by a reaction between organometallic compounds each including a first section including a metal alkoxide group including a plurality of alkoxy groups each having 1 to 3 carbon atoms, a second section including an alkoxyorganosiloxane structure portion, the second section being bonded to the first section, and a third section including an organic molecular chain or an organic silicon molecular chain or a reactive functional group, the third section being bonded to the second section;

the metal oxide-based core region is a region formed by condensation between the metal alkoxide groups of the first sections;

the intermediate region is a region formed by condensation between the alkoxyorganosiloxane structure portions of the second sections; and the surface region is a region including the organic molecular chains or the organic silicon molecular chains or the reactive functional groups of the third sections.

(4) The metal oxide-based fine particle according to the above item 3, wherein the first section is represented by formula (I):

[Formula 1]

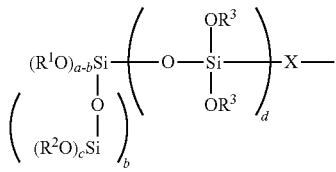

(I)

where $R^1$, $R^2$ and $R^3$ each independently represent an alkyl group having 1 to 3 carbon atoms, X represents a linking group, a represents 2 or 3, b represents 0, 1 or 2, c represents 2 or 3, and d represents 0 or a natural number, provided that a-b is 1 or more, one $R^1$ is directly bonded to a Si atom to which $R^1O$ is bonded when a is 2, and one $R^2$ is directly bonded to a Si atom to which $R^2O$ is bonded when c is 2;

the alkoxyorganosiloxane structure portion of the second section includes a unit represented by formula (IIa):

[Formula 2]

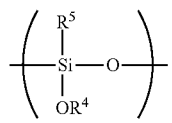

(IIa)

where $R^4$ represents an alkyl group having the number of carbon atoms equal to or more than the number of carbon atoms of $R^1$, $R^2$ and $R^3$, and $R^5$ represents an alkyl group having 1 to 10 carbon atoms, an aryl group having 6 to 10 carbon atoms, an alkenyl group having 2 to 10 carbon atoms, or an aralkyl group having 7 to 10 carbon atoms, and when there are a plurality of each of $R^4$ and $R^5$ in one molecule, $R^4$ and $R^5$ may each be the same as or different from each other; and the third section is represented by formula (III):

[Formula 3]

(III)

where $R^8$ represents an organic molecular chain or an organic silicon molecular chain or a reactive functional group, and Y represents a linking group.

(5) The metal oxide-based fine particle according to the above item 4, wherein $R^4$ is an alkyl group having one to four more carbon atoms than $R^1$, $R^2$ and $R^3$.

(6) The metal oxide-based fine particle according to the above item 4 or item 5, wherein $R^1$, $R^2$ and $R^3$ are a methyl group or an ethyl group.

(7) The metal oxide-based fine particle according to the above item 4 or item 5, wherein $R^1$, $R^2$ and $R^3$ are a methyl group or an ethyl group, and $R^4$ is an alkyl group having the same number of carbon atoms as $R^1$, $R^2$, and $R^3$.

(8) The metal oxide-based fine particle according to any one of the above item 4 to item 7, wherein d is 0.

(9) The metal oxide-based fine particle according to the above item 4, wherein the first section is represented by formula (IV):

[Formula 4]

(IV)

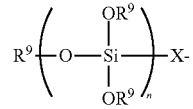

where $R^9$ represents an alkyl group having 1 to 3 carbon atoms, X represents a linking group, and n represents an integer of 3 or more.

(10) The metal oxide-based fine particle according to the above item 9, wherein $R^4$ is an alkyl group having one to four more carbon atoms than $R^9$.

(11) The metal oxide-based fine particle according to any one of the above item 4 to item 10, wherein $R^5$ is an alkyl group.

(12) The metal oxide-based fine particle according to any one of the above item 4 to item 11, wherein the molar ratio of a unit represented by formula (IIa) and another siloxane unit represented by formula (IIb) ([IIa]/([IIa]+[IIb])) is in the range of 0.2 to 1:

[Formula 5]

(IIb)

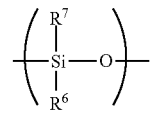

where $R^6$ and $R^7$ each independently represent an alkyl group having 1 to 10 carbon atoms, an aryl group having 6 to 10 carbon atoms, an alkenyl group having 2 to 10 carbon atoms, or an aralkyl group having 7 to 10 carbon atoms, and when there are a plurality of each of $R^6$ and $R^7$ in one molecule, $R^6$ and $R^7$ may each be the same as or different from each other.

(13) The metal oxide-based fine particle according to any one of the above item 4 to item 12, wherein the degree of polymerization of the alkoxyorganosiloxane structure portion of the second section is in the range of 2 to 30.

(14) The metal oxide-based fine particle according to any one of the above item 4 to item 12, wherein the degree of polymerization of the alkoxyorganosiloxane structure portion of the second section is in the range of 3 to 15.

(15) A resin filler including the metal oxide-based fine particle as recited in any one of the above item 1 to item 14.

(16) A resin composition including the metal oxide-based fine particle as recited in any one of the above item 1 to item 14 and a plastic.

(17) A method for manufacturing a metal oxide-based fine particle including a metal oxide-based core region, an intermediate region including an alkoxyorganosiloxane condensate structure, the intermediate region being formed on the outer periphery of the core region, and a surface region including an organic molecular chain or an organic silicon molecular chain or a reactive functional group, the method including:

forming the metal oxide-based core region by using an organometallic compound including a first section including a metal alkoxide group including a plurality of alkoxy groups each having 1 to 3 carbon atoms, a second section including an alkoxyorganosiloxane structure portion, the second section being bonded to the first section, and a third section including an organic molecular chain or an organic silicon molecular chain or a reactive functional group, the third section being bonded to the second section, and conducting condensation between the metal alkoxide groups of the first sections; and forming the intermediate region by condensation between the alkoxyorganosiloxane structure portions of the second sections, and forming the surface region including the organic molecular chains or the organic silicon molecular chains or the reactive functional groups located on the outer periphery of the intermediate region.

(18) The method for manufacturing a metal oxide-based fine particle, according to the above item 17, wherein the first section is represented by formula (I):

[Formula 6]

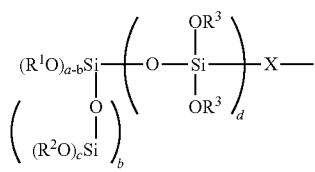

where $R^1$, $R^2$ and $R^3$ each independently represent an alkyl group having 1 to 3 carbon atoms, X represents a linking group, a represents 2 or 3, b represents 0, 1 or 2, c represents 2 or 3, and d represents 0 or a natural number, provided that a-b is 1 or more, one $R^1$ is directly bonded to a Si atom to which $R^1O$ is bonded when a is 2, and one $R^2$ is directly bonded to a Si atom to which $R^2O$ is bonded when c is 2;

the alkoxyorganosiloxane structure portion of the second section includes a unit represented by formula (IIa):

[Formula 7]

where $R^4$ represents an alkyl group having the number of carbon atoms equal to or more than the number of carbon atoms of $R^1$, $R^2$ and $R^3$, and $R^5$ represents an alkyl group having 1 to 10 carbon atoms, an aryl group having 6 to 10 carbon atoms, an alkenyl group having 2 to 10 carbon atoms, or an aralkyl group having 7 to 10 carbon atoms, and when there are a plurality of each of $R^4$ and $R^5$ in one molecule, $R^4$ and $R^3$ may each be the same as or different from each other; and the third section is represented by formula (III):
[Formula 8]

where $R^8$ represents an organic molecular chain or an organic silicon molecular chain or a reactive functional group, and Y represents a linking group.

According to the present invention, it is possible to provide a metal oxide-based fine particle effective in improving the strength of a plastic, and a method for manufacturing the same, and a resin composition with improved strength.

BEST MODE FOR CARRYING OUT THE INVENTION

An exemplary embodiment will be described below.

According to this exemplary embodiment, metal oxide-based fine particles with high functionality can be formed using an organic silicon compound, and by adding the metal oxide-based fine particles to a plastic, a resin composition with improved strength can be obtained.

Metal oxide-based fine particles with high functionality can be directly efficiently manufactured by using this organic silicon compound having a specific structure, unlike the above-described related art in which existing silica fine particles are treated using a surface treatment agent. The metal oxide-based fine particles have a layered structure having a metal oxide-based core region (hereinafter appropriately labeled as a "core"), an intermediate region (a region having an alkoxyorganosiloxane condensate structure), and a surface region (a region including an organic molecular chain or an organic silicon molecular chain or a reactive functional group), which are derived from the structure of the organic silicon compound. The function of this layered structure can significantly improve the strength, particularly toughness, of a plastic mixed with the metal oxide-based fine particles. Here, the "metal oxide-based core" means a core made of a metal oxide or a core having a structure close to that of a metal oxide.

In the exemplary embodiment, a compound including a first section including a metal alkoxide group having a plurality of alkoxy groups each having 1 to 3 carbon atoms, a second section including an alkoxyorganosiloxane structure portion, the second section being bonded to the first section, and a third section including an organic molecular chain or an organic silicon molecular chain or a reactive functional group, the third section being bonded to the second section can be used as the organic silicon compound.

This organic silicon compound is preferably a compound having three sections: a portion including an alkoxysilane group represented by the formula (I) (a first section), a specific alkoxyorganosiloxane portion including a unit represented by the formula (IIa) (a second section), and a portion including an organic molecular chain or an organic silicon molecular chain (hereinafter a "resin-compatible chain") or a reactive functional group represented by the formula (III) (a third section).

In the formation of the metal oxide-based fine particles, the alkoxysilane group of the first section react intermolecularly to form a core (a metal oxide-based core region), the alkoxy groups of the second section react intermolecularly to form an intermediate region (a region having an alkoxyorganosiloxane condensate structure), and the resin-compatible chain or the reactive functional group of the third section is located on the metal oxide-based fine particle surface. The effect of the compatibility of the resin-compatible chain on the metal oxide-based fine particle surface with a plastic, or the bonding between the reactive functional group on the metal oxide-based fine particle surface and a functional group of a plastic improves adhesion at the fine particle/plastic interface.

Between the organic silicon compounds, the reaction speed of the alkoxy groups of the alkoxysilane group of the first section is higher than the reaction speed of the alkoxy groups of the second section. By reacting the alkoxysilane group of the first section and then reacting the alkoxy groups of the second section intermolecularly, using this reactivity, metal oxide-based fine particles having a core, an intermediate region, and a surface region can be easily formed. The reason why the reaction speed of the alkoxy groups of the first section is higher than that of the alkoxy groups of the second section is that the alkoxy groups of the first section have fewer carbon atoms and higher density than the alkoxy groups of the second section, and are positioned at the tip of the molecule. When the alkoxy groups of the first section have one or two carbon atoms, the reactivity is significantly high, and therefore, even if the alkoxy groups of the second section have the same number of carbon atoms, the alkoxy groups of the first section can react preferentially, only due to the factors of the density of the alkoxy groups and the position at the tip of the molecule. Therefore, the target metal oxide-based fine particles can be formed.

In this organic silicon compound, association occurs around the site of the alkoxysilane group of the first section with the highest polarity and reactivity, in a solution, and the alkoxy groups of the alkoxysilane group condense intermolecularly to form a metal oxide-based core with high elasticity. Particularly, when the first section has alkoxysiloxane represented by the formula (IV), a metal oxide-based region is easily formed, and a core with high elasticity is obtained, because this alkoxysiloxane portion is a chain of previously polymerized siloxane units. Then, the alkoxy groups of the second section condense and crosslink to form an intermediate region with low elasticity, that is, stress relaxation properties, (for example, a silicone region) on the core. The remaining third section is located on the surface side, that is, a resin-compatible chain with high compatibility with a predetermined plastic, or a reactive functional group to be bonded to a functional group of a predetermined plastic is located on the surface of the metal oxide-based fine particle.

In this organic silicon compound, the reactivity of the alkoxy groups of the second section is lower than the reactivity of the alkoxy groups in the alkoxysilane group of the first section, and therefore, metal oxide-based fine particles can be formed easily and efficiently by such a two-stage reaction. Metal oxide-based fine particles with high functionality can be manufactured without performing a cumbersome surface treatment step for silica fine particles as in the above-described related art, and therefore, the productivity can be significantly improved.

In addition, the metal oxide-based fine particles formed from this organic silicon compound have the high adhesion of the fine particle surface to a predetermined plastic, stress relaxation properties due to the intermediate region, and high elasticity (high rigidity) due to the core, and therefore, the maximum stress and elongation at break of the plastic, the so-called toughness, can be significantly improved. Further, other mechanical properties, such as impact strength, can also be improved.

This exemplary embodiment will be described in more detail below.

The first section of this organic silicon compound can have, for example, a structure represented by the formula (I). In this case, a silica-based core region is formed as the core. Here, the "silica-based core" means a core made of silica or a core having a structure close to that of silica.

This organic silicon compound has an alkoxysilane group with high reactivity and polarity, as represented by the formula (I), as the first section. Particularly, the terminal alkoxysilane group has two or more alkoxy groups, preferably three alkoxy groups. Further, in terms of reactivity and the elasticity of the formed core, this organic silicon compound may have a terminal alkoxysilane group, and an alkoxysilane structure portion including a silicon atom bonded to the silicon atom of the terminal alkoxysilane group via oxygen (which corresponds to a case where b in the formula is 1 or 2). In addition, in terms of the ease of forming the core, and the elasticity of the core, this organic silicon compound may have an alkoxysiloxane unit (which corresponds to a case where d in the formula is not 0).

The alkoxy groups ($OR^1$, $OR^2$, and $OR^3$) of the first section may be the same as or different from each other. In addition, in terms of obtaining sufficient reactivity and elasticity of the core, these alkoxy groups are a methoxy group, an ethoxy group, or a propoxy group (that is, $R^1$, $R^2$, and $R^3$ are a methyl group, an ethyl group, or a propyl group), preferably a methoxy group or an ethoxy group, and particularly preferably a methoxy group. Here, the "propyl" includes "n-propyl" or "isopropyl."

The first section represented by the formula (I) can have, for example, any of the following structures:

(1) an alkoxysilane structure including a terminal silicon atom having two or more alkoxy groups (for example, a case where b=d=0), (2) a Si—O—Si structure including a terminal silicon atom having two alkoxy groups, an oxygen atom bonded to the terminal silicon atom, and a silicon atom bonded to the oxygen atom and having one or two alkoxy groups (for example, a case where b is 1 or 2, and d=0), and (3) a structure including the above structure (1) and an alkoxysilane unit (for example, a structure represented by the formula (IV): a case where a=3, b=0, $R^1$=$R^3$ (=$R^9$), and d≧2, which is the same as a case where a=c=3, b=1, $R^1$=$R^2$=$R^3$ (=$R^9$), and d≧1).

X in the formula (I) is any linking group to the second section and can have a structure according to a method for introducing the alkoxysilane group of the first section into the second section (alkoxyorganosiloxane portion). In other words, a linking portion according to the bonding structure formed by bonding the bonding functional group of alkoxyorganosiloxane for forming the second section with the bonding functional group of the first section, the bonding functional groups being described later, is formed. After the formation of the metal oxide-based fine particles, a structure in which the silicon atom of the intermediate region (silicone region) and the metal atom of the core are bonded via this linking portion can be obtained.

The linking group X may include a hydrocarbon group $R^{10}$ bonded to the silicon atom of the first section, and may be present between the silicon atom Si of the first section and a linking group X' connected to the silicon atom Si of the second section to form a linking bond represented by the following formula:

$$Si-R^{10}-X'-Si.$$

Examples of the hydrocarbon group $R^{10}$ include a linear or branched alkylene group having 1 to 5 carbon atoms. In addition, in the linking group X, an oxygen atom may be present between the silicon atom of the first section and the silicon atom of the second section to form a linking bond represented by the following formula:

$$Si-O-Si.$$

The first section can have various structures including a titanium atom, a zirconium atom, a zinc atom, or an aluminum atom replacing a silicon atom, as represented by the following formulas, instead of the structure represented by the formula (I). In a case where an aluminum atom is included, a in the formulas represents 1 or 2, b represents 0 or 1, and c represents 1 or 2. Other cases are the same as in the formula (I).

[Formula 9]

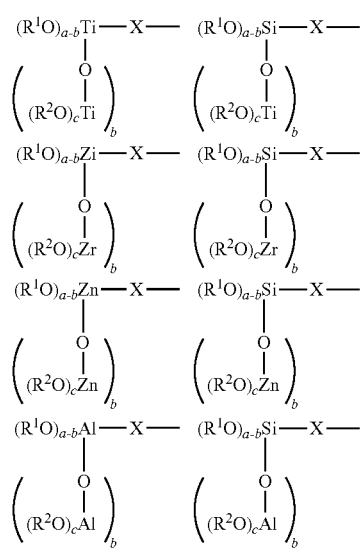

a: 1,2
b: 0,1
c: 1,2

In addition, the first section can have a structure having alkoxysiloxane represented by the formula (IV). In this case, in terms of obtaining sufficient reactivity and elasticity of the core, this alkoxy group ($OR^9$) is a methoxy group, an ethoxy group, or a propoxy group (that is, $R^9$ is a methyl group, an ethyl group, or a propyl group), preferably a methoxy group or an ethoxy group, and particularly preferably a methoxy group. Here, the "propyl" includes "n-propyl" or "isopropyl." In addition, the lower limit of the average degree of polymerization of this alkoxysiloxane portion is preferably 3 or more, more preferably 4 or more. The upper limit is not particularly limited, but is preferably 30 or less, more preferably 15 or less, and further preferably 10 or less. If this average degree of polymerization is too low, the effect of introducing the alkoxysiloxane portion, such as the effect of providing rigidity, is not sufficient. On the contrary, if this average degree of polymerization is too high, the formed metal oxide-based fine particles are too large, and accordingly, the dispersibility in a plastic and the effect of improving toughness may decrease.

The first section can have various structures including a titanium atom, a zirconium atom, a zinc atom, or an aluminum atom replacing a silicon atom, as represented by the following formulas, instead of the structure represented by the formula (IV).

[Formula 10]

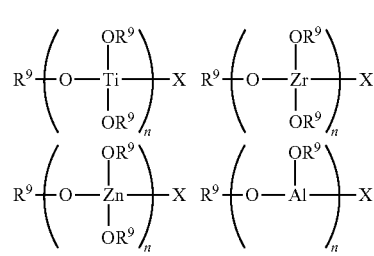

The alkoxy group ($OR^4$) of the second section of this organic silicon compound preferably has one to four more carbon atoms than the alkoxy groups ($OR^1$, $OR^2$, and $OR^3$) of the alkoxysilane group of the first section, in terms of making reactivity lower than that of the alkoxy groups, and more preferably two to four more carbon atoms, in terms of obtaining a more sufficient difference in reactivity. The alkoxy group of the second section preferably has 7 or less carbon atoms, and more preferably 5 or less carbon atoms, considering ensuring further sufficient reactivity. As described above, when the alkoxy groups of the first section have one or two carbon atoms, the desired difference in reactivity can be obtained even if the alkoxy group ($OR^4$) of the second section has the same number of carbon atoms as the alkoxy groups of the first section. Among the siloxane units having the alkoxy group ($OR^4$), $R^4$ may be the same as or different from each other. Such an alkoxy group can be selected from an ethoxy group, a propoxy group, a butoxy group, a pentyloxy group, a hexyloxy group, and a heptyloxy group. In other words, $R^4$ in the above formula can be selected from an ethyl group, a propyl group (an n-propyl group and an isopropyl group), a butyl group (an n-butyl group, an isobutyl group, a sec-butyl group, and a tert-butyl group), a linear or branched pentyl group, a linear or branched hexyl group, and a linear or branched heptyl group.

When the alkoxy groups of the first section are a methoxy group, $R^4$ of the second section can be a methyl group. In addition, in terms of further increasing the reactivity difference between the alkoxy groups of the first section and the alkoxy group of the second section, $R^4$ of the second section can be selected from alkyl groups having 2 to 5 carbon atoms, and is preferably selected from alkyl groups having 3 to 5 carbon atoms. A propyl group or a butyl group is more preferred, and a propyl group (particularly an n-propyl group) is most preferred. In addition, when the alkoxy groups of the first section are an ethoxy group, $R^4$ of the second section can be an ethyl group. In addition, in terms of further increasing the reactivity difference between the alkoxy groups of the first section and the alkoxy group of the second section, $R^4$ of the second section can be selected from alkyl groups having 3 to 6 carbon atoms, and is preferably selected from alkyl groups having 3 to 5 carbon atoms.

The organic group $R^5$ of the second section is an alkyl group having 1 to 10 carbon atoms, preferably an alkyl group having 1 to 5 carbon atoms, an aryl group having 6 to 10 carbon atoms, an alkenyl group having 2 to 10 carbon atoms, or an aralkyl group having 7 to 10 carbon atoms. When there are a plurality of siloxane units having $R^5$ in the molecule, $R^3$ may be the same as or different from each other among the siloxane units. Examples of the alkyl group having 1 to 10 carbon atoms include a methyl group, an ethyl group, a propyl group (an n-propyl group and an isopropyl group), a butyl group (an n-butyl group, an isobutyl group, a sec-butyl group, and a tert-butyl group), a linear or branched pentyl group, and a cycloalkyl group, such as a cyclohexyl group. Examples of the aryl group having 6 to 10 carbon atoms include a phenyl group, a tolyl group, a xylyl group, and a naphthyl group. Examples of the alkenyl group having 2 to 10 carbon atoms include a vinyl group, an allyl group, a butenyl group, a hexenyl group, and an octenyl group. Examples of the aralkyl group having 7 to 10 carbon atoms include those in which the above alkyl group has the above aryl group as a substituent.

The organic groups $R^6$ and $R^7$ of the second section are each independently an alkyl group having 1 to 10, preferably 1 to 5 carbon atoms, an aryl group having 6 to 10 carbon atoms, an alkenyl group having 2 to 10 carbon atoms, or an aralkyl group having 7 to 10 carbon atoms. When there are a plurality of siloxane units having $R^6$ and $R^7$ in the molecule, $R^6$ and $R^7$ may each be the same as or different from each other among the siloxane units. Examples of the alkyl group, the aryl group, the alkenyl group, or the aralkyl group of $R^6$ and $R^7$ include the above alkyl groups, aryl groups, alkenyl groups, or aralkyl groups illustrated for $R^5$.

The lower limit of the average degree of polymerization of the siloxane portion of the second section of this organic silicon compound is 2 or more, preferably 3 or more, and more preferably 4 or more. The upper limit is not particularly limited, but is preferably 30 or less, more preferably 15 or less, and further preferably 10 or less. If this average degree of polymerization is too low, the stress relaxation effect is not sufficient. On the contrary, if this average degree of polymerization is too high, the formed metal oxide-based fine particles are too large, and accordingly, the dispersibility in a plastic and the effect of improving toughness may decrease.

The siloxane portion of the second section can have a structure in which an alkoxy group and an organic group derived from an alkoxysilane, a raw material, are bonded to its terminal silicon atom. Examples of these alkoxy group and organic group include those similar to the alkoxy group and organic group of the siloxane unit of the second section described above. The first section or the third section may be introduced into a terminal siloxane unit having this terminal silicon atom.

$R^8$ of the third section is a resin-compatible chain or a reactive functional group, and is a chain compatible with a predetermined plastic to which the metal oxide-based fine particles formed from this organic silicon compound are added, or a functional group that can be bonded to a functional group of the predetermined plastic. This third section can have any structure, considering compatibility or bonding reactivity according to the type of the predetermined plastic. This resin-compatible chain is an organic molecular chain or an organic silicon molecular chain. The organic silicon molecular chain means a siloxane bond chain (organopolysiloxane) or one in which an organic molecule is bonded to silicon or siloxane. These desirably have low reactivity or do not react in the condensation reactions of the first and second sections.

Such a third section is bonded to the siloxane unit of the second section via a linking group Y. This linking group Y can have a structure according to a method for introducing the third section into the second section. In other words, a linking portion according to the bonding structure formed by bonding the bonding functional group of alkoxyorganosiloxane for forming the second section with the bonding functional group of the third section, the bonding functional groups being described later, is formed. After the formation of the metal oxide-based fine particles, a structure in which the resin-compatible chain or the reactive functional group and the silicon atom of the intermediate region (for example, a silicone region) are bonded via this linking portion can be obtained.

In this organic silicon compound, the first section has higher polarity than other sections. Therefore, as described above, association occurs around the alkoxysilane group of the first section, in a solution, and the alkoxy groups of the alkoxysilane group condense intermolecularly to form a core made of a silicon oxide-based material with high elasticity. The alkoxy groups of the second section have lower reaction speed and lower density than the alkoxy groups in the alkoxysilane group of the first section. Accordingly, using this, a condensation reaction can be suppressed in the formation of the core, and the alkoxy groups of the second section can condense and crosslink after the core is formed. The intermediate region formed on the outer periphery of the core in this manner has a structure with low polarity derived from the siloxane unit in the second section, and accordingly has low elasticity, that is, stress relaxation properties. With the formation of this intermediate region, the resin-compatible chain or the reactive functional group derived from the third section is located on the most outside of the formed metal oxide-based fine particle, and a surface region that can be compatibilized with and bonded to a plastic is formed.

The alkoxyorganosiloxane portion of the second section of this organic silicon compound may be formed of a chain of units of the formula (IIa) alone, or may be formed of a chain of units of the formula (IIa) and other siloxane units. Units represented by the formula (IIb) are preferred as the other siloxane units. The content of the units of the formula (IIa) in the alkoxyorganosiloxane portion of the second section is preferably 20 mole % or more, more preferably 40 mole % or more. When the other siloxane units are units of the formula (IIb), the molar ratio of the units of the formula (IIa) and the units of the formula (IIb) ([IIa]/([IIa]+[IIb])) can be set in the range of 0.2 to 1 and is preferably in the range of 0.4 to 1. If the content ratio of the units of the formula (IIa) is too low, the reactivity during the formation of the metal oxide-based fine particles decreases, and a sufficient crosslinked structure may not be formed.

The R/Si ratio (the molar ratio of organic groups R directly bonded to a siloxane silicon atom and Si atoms) of the intermediate region of the metal oxide-based fine particle formed from such an organic silicon compound can be set in the range of 1 to 1.8 and is preferably in the range of 1 to 1.6. If this R/Si ratio is too high, a sufficient crosslinked structure is not formed, and therefore, the desired effect may not be obtained. The organic groups R directly bonded to a siloxane silicon atom include $R^3$, $R^6$, and $R^7$ in the formulas.

The manufacture of this organic silicon compound can be performed by introducing the first section (alkoxysilane group-containing portion) and the third section (resin-compatible chain or reactive functional group-containing portion) into an alkoxyorganosiloxane corresponding to the second section.

For example, it is possible to react alkoxyorganopolysiloxane (alkoxy silicone) having the structure of the second section with a compound having the third section (a compound for introducing the third section) and then react the alkoxyorganopolysiloxane with a compound having the first section (a compound for introducing the first section). Alternatively, the order of these reactions may be reversed. It is also possible to mix these compounds together and react them when the combination of the reactive functional groups can be optimized.

In the manufacture of this organic silicon compound, an organic silicon compound having a functional group that can react with alkoxyorganosiloxane (a bonding functional group), and an alkoxysilane group having a plurality of alkoxy groups that corresponds to the structure represented by the formula (I), can be used as the compound for introducing the first section.

An alkoxyorganosilane compound having a bonding functional group (for example, trialkoxyorganosilane having a bonding functional group, and dialkoxyorganosilane having a bonding functional group) can be used as such a compound for introducing the first section. The alkoxy groups of this alkoxyorganosilane compound are a methoxy group, an ethoxy group, or a propoxy group. Part of the alkoxy groups may be substituted with a halogen atom, such as a chlorine atom. Examples of the bonding functional group of this alkoxyorganosilane compound include an isocyanate group, an epoxy group, a carboxyl group, an amino group, a thiol group, a vinyl group, a methacryl group, a hydroxyl group, and a hydrosilyl group. The bonding functional group need only be a group that can react with a functional group in the unit of alkoxyorganosiloxane. Specific examples of the alkoxyorganosilane compound having such a bonding functional group include 3-isocyanatepropyltrimethoxysilane, 3-isocyanatepropyltriethoxysilane, 3-glycidoxypropyltrimethoxysilane, 3-glycidoxypropyltriethoxysilane, carboxymethyltrimethoxysilane, carboxymethyltriethoxysilane, 3-aminopropyltrimethoxysilane, 3-aminopropyltriethoxysilane, 3-mercaptopropyltrimethoxysilane, 3-mercaptopropyltriethoxysilane, vinyltrimethoxysilane, vinyltriethoxysilane, 3-methacryloxypropyltrimethoxysilane, and 3-methacryloxypropyltriethoxysilane.

Particularly, when the compound for introducing the first section has alkoxysiloxane represented by the formula (IV), examples of the bonding functional group include an alkoxy group, a hydroxyl group, an amino group, an epoxy group, a carboxyl group, and an isocyanate group. This hydroxyl group can be formed by the reaction of an alkoxy group. The functional groups such as an amino group, an epoxy group, a carboxyl group, and an isocyanate group can be introduced by reacting compounds having this functional group and a group that can react with an alkoxy group (or a hydroxyl group), with the alkoxy group (or hydroxyl group) in the alkoxysiloxane. Examples of the alkoxysiloxane having such a bonding functional group include methoxy silicone, ethoxy silicone, and propyloxy silicone. In these alkoxysiloxanes, their alkoxy group can be used as the bonding functional group, as it is, or a hydroxyl group converted from this alkoxy group can be used as the bonding functional group, and thus the step for introducing the bonding functional group can be omitted or simplified.

Alkoxyorganosiloxane, such as alkoxy silicone including a siloxane unit that has an organic group (an alkyl group or the like) and an alkoxy group having lower reactivity than the alkoxy groups in the alkoxysilane group of the first section, can be used as the compound for forming the second section. This alkoxyorganosiloxane has a functional group to be bonded to the bonding functional group of the compound for introducing the first section, and a functional group to be bonded to the compound for forming the third section.

The alkoxy group of the alkoxyorganosiloxane for forming the second section preferably has one to four more carbon atoms than the alkoxy groups of the alkoxysilane group of the first section. In addition, the alkyl group in this siloxane unit has 1 to 10 carbon atoms, preferably 1 to 5 carbon atoms. This alkyl group may be replaced by an aryl group having 6 to 10 carbon atoms, an alkenyl group having 2 to 10 carbon atoms, or an aralkyl group having 7 to 10 carbon atoms. Particularly, when $R^1$, $R^2$, and $R^3$ of the first section are a methyl group or an ethyl group, $R^4$ of the second section may be an alkyl group having the same number of carbon atoms as $R^1$, $R^2$, and $R^3$. For the proportion of the alkoxy groups and the organic groups (alkyl groups, aryl groups, alkenyl groups, or aralkyl groups) directly bonded to a siloxane silicon atom in this alkoxyorganosiloxane, the molar ratio of the alkoxy groups to the total number of these can be set to 10% or more and is preferably 20% or more. In addition, the molar ratio of the alkoxy groups can be set to 80% or less and is preferably 60% or less, more preferably 50% or less. If the proportion of the alkoxy groups is too low, the reactivity during the formation of the metal oxide-based fine particles decreases, and a sufficient crosslinked structure may not be formed. If this proportion is too high, the crosslinking density is too high, and the stress relaxation properties may be insufficient.

Examples of the functional group (bonding functional group) in the alkoxyorganosiloxane for forming the second section, which is to be bonded to the compound for introducing the first section or the compound for introducing the third section, include an alkoxy group, a hydroxyl group, an amino group, an epoxy group, a carboxyl group, and an isocyanate group. This hydroxyl group can be formed by the reaction of an alkoxy group. The functional group such as an amino group, an epoxy group, a carboxyl group, and an isocyanate group can be introduced by reacting compounds having this functional group and a group that can react with an alkoxy group (or a hydroxyl group), with the alkoxy group (or hydroxyl group) in the alkoxyorganosiloxane. Examples of the alkoxyorganosiloxane having such a bonding functional group include propyloxymethyl silicone, propyloxyhydroxymethyl silicone, and propyloxyhydroxyphenylmethyl silicone. In these alkoxyorganopolysiloxanes, their alkoxy group can be used as the bonding functional group, as it is, or a hydroxyl group converted from this alkoxy group can be used as the bonding functional group, and thus the step for introducing the bonding functional group can be omitted or simplified.

The compound for introducing the third section is an organic compound or an organic silicon compound having a resin-compatible chain that can be compatible with a predetermined plastic to which the metal oxide-based fine particles formed from this organic silicon compound are added, or a functional group (a reactive functional group) that can react with this plastic, and a functional group (a bonding functional group) that can be bonded to the second section. The structure of these compounds can be determined according to the molecular structure of the predetermined plastic.

Examples of the bonding functional group that can be bonded to the second section include an isocyanate group, an epoxy group, a carboxyl group, an amino group, a thiol group, a vinyl group, a methacryl group, a hydroxyl group, and a hydrosilyl group. The bonding functional group need only be a group that can react with a functional group in the unit of alkoxyorganosiloxane.

In the compound for introducing the third section, having the resin-compatible chain, it is preferred that the resin-compatible chain portion has a portion common or similar to the structure of the predetermined plastic, for example, a chain of the same or similar units to that of the plastic. In terms of obtaining a sufficient compatibility effect, the number average molecular weight of this resin-compatible chain portion is preferably smaller than the average molecular weight of the predetermined plastic, more preferably 50% or less, and is preferably 1% or more of the number average molecular weight of the predetermined plastic, more preferably 5% or more. In addition, the number average molecular weight of this resin-compatible chain portion is preferably 100 or more, more preferably 200 or more, and is preferably 10000 or less, more preferably 2000 or less. If this average molecular weight is too low, a sufficient compatibility effect may not be obtained. If this average molecular weight is too high, the surface layer of the metal oxide-based fine particles is too thick, and accordingly, the metal oxide-based fine particles aggregate easily, and sufficient dispersibility may not be obtained.

There is a case where this resin-compatible chain need not have a structure common or similar to that of the predetermined plastic when the compatibility with the predetermined plastic is sufficient. In this case, the solubility parameter (SP value) of the resin-compatible chain is preferably the same as or close to the SP value of the predetermined plastic. Specifically, the solubility parameter of the resin-compatible chain is preferably in the range of 70% or more and 130% or less of the SP value of the plastic.

Examples of the reactive functional group that can react with the predetermined plastic include an alkoxy group, a hydroxyl group, an epoxy group, an amino group, a carboxyl group, an isocyanate group, a thiol group, a vinyl group, a methacryl group, and a hydrosilyl group.

When the predetermined plastic is polyester, examples of the compound for introducing the third section include polyester derivatives, polycaprolactone, polyethylene glycol, epoxy silicone, and polyoxyalkylene silicone. When the predetermined plastic is an epoxy resin, examples of the compound for forming the third section include epoxy resin derivatives, phenolic resin derivatives, carboxy silicone, amino silicone, hydroxy silicone, epoxy silicone, polyoxyalkylene silicone, and polycaprolactone. When the predetermined plastic is polyolefin, examples of the compound for forming the third section include polyolefin derivatives. When the predetermined plastic is polystyrene, examples of the compound for forming the third section include polystyrene derivatives and acrylonitrile derivatives. When the predetermined plastic is a cellulosic resin, for example, cellulose acetate, examples of the compound for forming the third section include polycaprolactone.

For example, it is possible to manufacture a resin composition (plastic composite material) by forming metal oxide-based fine particles from this organic silicon compound, adding the metal oxide-based fine particles to a plastic, and dispersing the metal oxide-based fine particles, in the following manner.

Metal oxide-based fine particles can be formed from this organic silicon compound by adding this organic silicon compound to a solvent, in which this organic silicon compound can be dissolved or dispersed, to make a mixed solution, and adding an acid catalyst or a base catalyst, and further an appropriate amount of water, as required, to this solution under suitable conditions, for example, heating. Then, a composite material can be formed by adding a predetermined plastic to this solution, dissolving or dispersing the predetermined plastic, and then evaporating the solvent. Alternatively, a composite material can be formed by evaporating this solvent, then adding a plastic, and mixing the plastic by heating and melting. Further, under specific conditions, it is also possible to manufacture a composite material by adding this organic silicon compound to a plastic in liquid form made by dispersion, melting, or the like, and forming metal oxide-based fine particles in the presence of the plastic.

The above solvent is not particularly limited as long as this organic silicon compound can be dissolved or dispersed in it. For example, alcohols, such as methanol and ethanol, ketones, such as acetone and 2-butanone, tetrahydrofuran, dimethylformamide, pyridine, and the like, which are hydrophilic solvents, can be used. Hydrophobic solvents, such as chloroform and dichloromethane, can also be used. Further, mixed solvents of these can also be used.

Examples of the above acid catalyst include organic acids, such as formic acid and acetic acid, and inorganic acids, such as hydrochloric acid. Examples of the base catalyst include ammonia, triethylamine, dimethylamine, ethylenediamine, and butylamine.

In terms of obtaining a sufficient effect of improving resin strength, the particle diameter of the metal oxide-based fine particles according to the present invention is preferably in the range of 1 nm to 10 µm, more preferably in the range of 1 nm to 1000 nm, further preferably in the range of 5 nm to 500 nm, and particularly preferably in the range of 5 to 100 nm.

The plastic to which the metal oxide-based fine particles according to the present invention are added is not particularly limited, but can be preferably uniformly mixed with the metal oxide-based fine particles according to the present invention (or the organic silicon compound itself) in a solution or in a dispersion or melt of the plastic. Examples of the plastic include polyesters, such as polylactic acid, polybutylene succinate, and polycarbonate, polyolefins, such as polypropylene and polyethylene, epoxy resins, phenolic resins, polystyrene, polyamide, polyurethane, polyimide, and cellulosic resins, particularly cellulose acetate.

The amount of the metal oxide-based fine particles according to the present invention added to the plastic is preferably 0.1% or more by weight, more preferably 1% or more by weight, and further preferably 3% or more by weight, in terms of obtaining a sufficient addition effect. On the other hand, the amount is preferably 70% or less by weight, more preferably 50% or less by weight, and further preferably 10% or less by weight, in terms of not largely impairing the properties of the plastic, such as moldability.

Additives usually used may be further added to the resin composition containing the metal oxide-based fine particles. Examples of these additives include a fibrous or particulate filler of an organic substance or an inorganic substance, a flame retardant, a flexibility-providing agent, a plasticizer, and a weather-resistant agent. The method for mixing the additives into this resin composition is not particularly limited. Examples of the method include mixing by a publicly known mixer, for example, a tumbler, a ribbon blender, or a single-screw or twin-screw kneader, and melting and mixing by an extruder, a roll, or the like.

The resin composition containing the metal oxide-based fine particles can be processed into molded articles for electric and electronic equipment applications, such as enclosures for electric appliances, building material applications, automobile part applications, daily necessity applications, medical applications, agricultural applications, and the like by usual molding methods, such as a compression molding method, an injection molding method, a film molding method, a blow molding method, and an expansion molding method.

EXAMPLES

The present invention will be described below in more detail by giving Examples together with Comparative Examples.

Organic silicon compounds and metal oxide-based fine particles (silica-based fine particles) were manufactured according to the following synthesis examples.

Synthesis Example 1

Synthesis of Organic Silicon Compound 1

As an example of the organic silicon compound according to the present invention, a compound in which a group represented by the following chemical formula (B) corresponding to the first section, and a group represented by the following chemical formula (C) corresponding to the third section were bonded to alkoxyorganopolysiloxane represented by the following chemical formula (A), the propyl group portions of its propoxy groups being replaced, was synthesized. Me in the formulas represents a methyl group, Pr represents a propyl group, and Bu represents a butyl group.

[Formula 11]

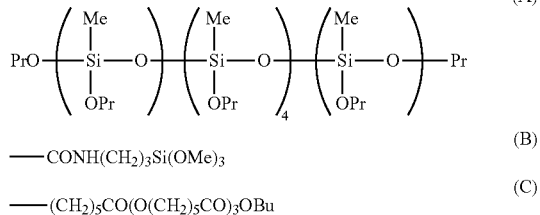

(A)

——CONH(CH$_2$)$_3$Si(OMe)$_3$  (B)

——(CH$_2$)$_5$CO(O(CH$_2$)$_5$CO)$_3$OBu  (C)

The organic silicon compound 1 was obtained by preparing alkoxyorganopolysiloxane corresponding to the second section, introducing a resin-compatible chain into this polysiloxane, and then introducing an organic group containing an alkoxysilane group. Specifically, the organic silicon compound was synthesized in the following order of steps:
(a) propyloxymethyl silicone was synthesized,
(b) terminal hydroxy-modified polycaprolactone was synthesized,
(c) the propyloxymethyl silicone and the terminal hydroxy-modified polycaprolactone were bonded to form a silicone-bonded substance,
(d) a silanol group was formed in the propyloxymethyl silicone in the above bonded substance, and
(e) the silanol group of the propyloxymethyl silicone in the above bonded substance and isocyanatepropyltrimethoxysilane were bonded.

A description will be given below in this order of steps.
Step (a)

22.0 g (100 mmol) of methyltripropoxysilane (LS-3630 manufactured by Shin-Etsu Chemical Co., Ltd.), 60 g (1 mol) of 1-propanol, and 9.0 g of an aqueous hydrochloric acid solution with its pH adjusted to 2.5 were added to a 200 ml eggplant flask and stirred in the air at 20° C. for 3 hours. Then, 2.4 g of a 0.01 M aqueous sodium hydroxide solution was added to neutralize the hydrochloric acid. Then, 300 g of magnesium sulfate (anhydrous) was added, and dehydration and drying were performed for 2 hours. Then, the salt and the magnesium sulfate were removed by filtration, and then, the 1-propanol and the unreacted methyltripropoxysilane were distilled off, using a rotary evaporator, to obtain linear propyloxymethyl silicone. The yield was 80%. From $^1$H-NMR, it was confirmed that the number average molecular weight was 800 (average degree of polymerization: 6).
Step (b)

As shown in the following reaction formula, ε-caprolactone (PLACCE M manufactured by DAICEL CHEMICAL INDUSTRIES, LTD.) was ring-opening polymerized, using 1-butanol as an initiator, in the following manner, to synthesize terminal hydroxy-modified polycaprolactone.

22.8 g (200 mmol) of the ε-caprolactone, 5.0 g (67 mmol) of 1-butanol, and 6.8×10$^{-3}$ g of tin octylate as a catalyst were added to a 100 ml eggplant flask and stirred under a nitrogen atmosphere at 150° C. for 10 hours. Then, the unreacted ε-caprolactone and the 1-butanol were removed by distillation by heating under reduced-pressure (150° C., 10 mmHg (1.33 kPa)). From $^1$H-NMR, an oligomer having a number average molecular weight of 550 was confirmed. The yield was 95%.

[Formula 12]

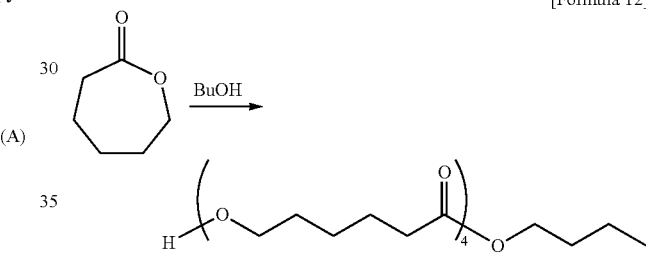

Step (c)

The above propyloxymethyl silicone and terminal hydroxy-modified polycaprolactone were bonded by a dealcoholization reaction between the propyloxy group and the hydroxyl group in the following manner.

5.4 g of the propyloxymethyl silicone, 3.3 g (6 mmol) of the terminal hydroxy-modified polycaprolactone, 6.0×10$^{-2}$ g (6 mmol) of methanesulfonic acid as a catalyst, and 20 ml of toluene were added to a 100 ml three-neck eggplant flask. The flask was equipped with a reduced-pressure distillation apparatus and a dropping funnel. The materials were stirred for 5 hours, while toluene was dropped at a speed of 1 ml per minute, and produced 1-propanol and the toluene were distilled off under a reduced pressure of 150 mmHg (20 kPa) at 60° C. Then, 4.9×10$^{-2}$ g (6 mmol) of pyridine was added to neutralize the methanesulfonic acid. The salt was removed by filtration, and then, the remaining 1-propanol was distilled off, using a rotary evaporator. From $^1$H-NMR, the reaction rate was 98%.
Step (d)

Part of the propyloxy groups of the above bonded substance were converted to a silanol group by hydrolysis in the following manner.

3.8 g of the above bonded substance, 1.5 g of an aqueous hydrochloric acid solution with its pH adjusted to 2.5, and 30 ml of acetone were added to a 100 ml Erlenmeyer flask and stirred in the air at 20° C. for 1 hour. Then, 0.4 g of a 0.01 M aqueous sodium hydroxide solution was added to neutralize the hydrochloric acid. 50 g of magnesium sulfate (anhydrous)

was added, and dehydration and drying were performed for 2 hours. Then, the salt and the magnesium sulfate were removed by filtration, and the acetone was distilled off, using a rotary evaporator. From $^1$H-NMR, the conversion rate to silanol group was calculated as 13% (on average, one silanol group was formed in one molecule). The silanol group was formed, while a condensation reaction due to the reaction between silanol groups was sufficiently suppressed.

Step (e)

The above bonded substance in which the silanol group was formed and isocyanatepropyltrimethoxysilane (SII6456.0 manufactured by AZmax Co.) were bonded by a reaction between the silanol group and the isocyanate group in the following manner.

3.4 g of the above bonded substance, 0.5 g (2.5 mmol) of the isocyanatepropyltrimethoxysilane, and $1.0 \times 10^{-3}$ g of tin octylate as a catalyst were added to a 20 ml eggplant flask and allowed to stand under a nitrogen atmosphere at 20° C. for 24 hours. From $^1$H-NMR, the reaction rate was 90%.

The number average molecular weight of the obtained organic silicon compound was measured by GPC (gel permeation chromatography, "10A-VP" manufactured by SHIMADZU CORPORATION, columns: two GPC-80MC and one GPC-8025C, developing solvent: chloroform, standard sample: polystyrene) to be 1700.

Synthesis Example 2

Manufacture of Silica-Based Fine Particles 1

Metal oxide-based fine particles (silica-based fine particles) were manufactured from the above organic silicon compound by the following two-stage step:
(1) the sol-gel reaction of the methoxy groups of the first sections (the formation of a core), and
(2) the sol-gel reaction of the propyloxy groups of the second sections (the formation of an intermediate region, and as a result, the formation of a surface layer derived from the third sections).

A description will be given below in this order of steps.

Step (1)

1.9 g of the above organic silicon compound, 1.8 g (100 mmol) of pure water, 1.6 g of 28% ammonia water, and 10 ml of acetone were added to a 50 ml eggplant flask and allowed to stand in the air at 20° C. for 48 hours. Then, produced methanol, the water, the ammonia, and the acetone were distilled off, using a rotary evaporator. From $^1$H-NMR, it was confirmed that the reaction rate of the methoxy groups was 83%, and the reaction of the propyloxy groups hardly proceeded (5% or less).

Step (2)

A 200 ml eggplant flask was equipped with a cooling tube. 0.5 g of the condensation substance obtained in the step (1), 100 ml of chloroform, $5.0 \times 10^{-2}$ g (2.8 mmol) of pure water, and 5 ml of acetone were added to the eggplant flask, and stirred for 10 hours, while the chloroform was boiling-point-refluxed in the air at 70° C. Then, produced propanol, the water, and part of the chloroform were distilled off, using a rotary evaporator, to obtain a chloroform dispersion solution of metal oxide-based fine particles. From $^1$H-NMR, it was confirmed that the reaction rate of the propyloxy groups of the second section of the silicon compound was 85%.

From the observation of the obtained metal oxide-based fine particles by an STEM (scanning transmission electron microscope, HD-2300 manufactured by Hitachi High-Technologies Corporation), the average particle diameter of the metal oxide-based fine particles was about 30 nm. In this STEM observation, the diameters of randomly selected 10 fine particles were measured, and their average value was calculated as the average particle diameter.

Example 1

100 g of polylactic acid (TE-4000 manufactured by UNITIKA LTD., number average molecular weight: $9.1 \times 10^5$) as an aliphatic polyester resin was added to and mixed in 500 ml of chloroform containing 5 g of the above metal oxide-based fine particles. Then, while the mixture was heated at 50° C., the pressure was reduced by an aspirator to remove the solvent to obtain a polylactic acid resin composition containing 5% by weight of the metal oxide-based fine particles.

This resin composition was heated and melted on a hot plate at 180° C. and poured into a mold to fabricate test pieces with a thickness of 2 mm, a length of 40 mm, and a width of 25 mm. Then, the bending strength and elongation (bending strain) of the test pieces were measured by the method defined in the standard JIS K7171. For a sample that did not break at the point of time of maximum stress, the measurement was continued until the elongation was 10%. Then, the average of the measured values of five test pieces was obtained, and the value was rounded off to the nearest whole number. The evaluation results are shown in Table 1.

Synthesis Example 3

Synthesis of Organic Silicon Compound 2

As an example of the organic silicon compound according to the present invention, a compound in which a group represented by the following chemical formula (E) corresponding to the first section, and a group represented by the following chemical formula (C) corresponding to the third section were bonded to alkoxyorganopolysiloxane represented by the following chemical formula (D), the ethyl group portions of its ethoxy groups being replaced, was synthesized. Me in the formulas represents a methyl group, Et represents an ethyl group, and Bu represents a butyl group.

[Formula 13]

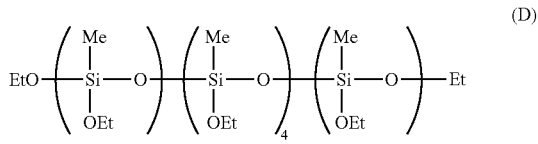

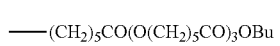

The organic silicon compound 2 was obtained by preparing alkoxyorganopolysiloxane corresponding to the second section, introducing a resin-compatible chain into this polysiloxane, and then introducing an organic group containing an alkoxysilane group. Specifically, the organic silicon compound was synthesized in the following order of steps:
(a) ethoxymethyl silicone was synthesized,
(b) terminal hydroxy-modified polycaprolactone was synthesized,
(c) the ethoxymethyl silicone and the terminal hydroxy-modified polycaprolactone were bonded to form a silicone-bonded substance, (d) a silanol group was formed in the ethoxymethyl silicone in the above bonded substance, and
(e) the silanol group of the ethoxymethyl silicone in the above bonded substance and isocyanatepropyltriethoxysilane were bonded.

A description will be given below in this order of steps.

Step (a)

18 g (100 mmol) of methyltriethoxysilane (LS-1890 manufactured by Shin-Etsu Chemical Co., Ltd.), 46 g (1 mol) of ethanol, and 3.0 g of an aqueous hydrochloric acid solution with its pH adjusted to 2.5 were added to a 200 ml eggplant flask and stirred in the air at 20° C. for 3 hours. Then, 0.8 g of a 0.01 M aqueous sodium hydroxide solution was added to neutralize the hydrochloric acid. Then, 300 g of magnesium sulfate (anhydrous) was added, and dehydration and drying were performed for 2 hours. Then, the salt and the magnesium sulfate were removed by filtration, and then, the ethanol and the unreacted methyltriethoxysilane were distilled off, using a rotary evaporator, to obtain linear ethoxymethyl silicone. The yield was 80%. From $^1$H-NMR, it was confirmed that the number average molecular weight was 700 (average degree of polymerization: 6).

Step (b)

Terminal hydroxy-modified polycaprolactone was prepared as in Synthesis Example 1.

Step (c)

The above ethoxymethyl silicone and terminal hydroxy-modified polycaprolactone were bonded by a dealcoholization reaction between the ethoxy group and the hydroxyl group in the following manner.

8.4 g of the ethoxymethyl silicone, 6.6 g (12 mmol) of the terminal hydroxy-modified polycaprolactone, $1.2 \times 10^{-1}$ g (12 mmol) of methanesulfonic acid as a catalyst, and 20 ml of toluene were added to a 100 ml three-neck eggplant flask. The flask was equipped with a reduced-pressure distillation apparatus and a dropping funnel. The materials were stirred for 5 hours, while toluene was dropped at a speed of 1 ml per minute, and produced ethanol and the toluene were distilled off under a reduced pressure of 150 mmHg (20 kPa) at 60° C. Then, $9.5 \times 10^{-2}$ g (12 mmol) of pyridine was added to neutralize the methanesulfonic acid. The salt was removed by filtration, and then, the remaining ethanol and toluene were distilled off, using a rotary evaporator. From $^1$H-NMR, the reaction rate was 98%.

Step (d)

Part of the ethoxy groups of the above bonded substance were converted to a silanol group by hydrolysis in the following manner.

13 g of the above bonded substance, 2.0 g of an aqueous hydrochloric acid solution with its pH adjusted to 2.5, and 120 ml of acetone were added to a 200 ml Erlenmeyer flask and stirred in the air at 20° C. for 1 hour. Then, 0.4 g of a 0.01 M aqueous sodium hydroxide solution was added to neutralize the hydrochloric acid. 50 g of magnesium sulfate (anhydrous) was added, and dehydration and drying were performed for 2 hours. Then, the salt and the magnesium sulfate were removed by filtration, and the acetone was distilled off, using a rotary evaporator. From $^1$H-NMR, the conversion rate to silanol group was calculated as 13% (on average, one silanol group was formed in one molecule). The silanol group was formed, while a condensation reaction due to the reaction between silanol groups was sufficiently suppressed.

Step (e)

The above bonded substance in which the silanol group was formed and isocyanatepropyltriethoxysilane (LS-3415 manufactured by Shin-Etsu Chemical Co., Ltd.) were bonded by a reaction between the silanol group and the isocyanate group in the following manner.

9.0 g of the above bonded substance, 1.8 g (7.5 mmol) of the isocyanatepropyltriethoxysilane, and $2.7 \times 10^{-3}$ g of tin octylate as a catalyst were added to a 50 ml eggplant flask and stirred under a nitrogen atmosphere at 20° C. for 24 hours. From $^1$H-NMR, the reaction rate was 90%.

The number average molecular weight of the obtained organic silicon compound was measured by GPC (gel permeation chromatography, "10A-VP" manufactured by SHIMADZU CORPORATION, columns: two GPC-80MC and one GPC-8025C, developing solvent: chloroform, standard sample: polystyrene) to be 1600.

Synthesis Example 4

Manufacture of Silica-Based Fine Particles 2

Silica-based fine particles 2 were manufactured from the organic silicon compound 2 in the above Synthesis Example 3 by the following two-stage step:
(1) the sol-gel reaction of the ethoxy groups of the first sections (the formation of a core), and
(2) the sol-gel reaction of the ethoxy groups of the second sections (the formation of an intermediate region, and as a result, the formation of a surface layer derived from the third sections).

A description will be given below in this order of steps.

Step (1)

9.5 g of the above organic silicon compound, 9.0 g (0.5 mol) of pure water, 16 g of 29% ammonia water, and 30 ml of acetone were added to a 200 ml eggplant flask and stirred in the air at 20° C. for 12 hours.

Step (2)

16 g of 29% ammonia water and 200 ml of acetone were added to the solution obtained in the step (1) and stirred in the air at 20° C. for 24 hours. Then, produced ethanol, the ammonia water, and the acetone were distilled off, using a rotary evaporator. From $^1$H-NMR, it was confirmed that the reaction rate of the ethoxy groups of the silicon compound was 85%.

From the observation of the obtained silica-based fine particles by an STEM (scanning transmission electron microscope, HD-2300 manufactured by Hitachi High-Technologies Corporation), the average particle diameter of the silica-based fine particles was about 25 nm. In this STEM observation, the diameters of randomly selected 10 fine particles were measured, and their average value was calculated as the average particle diameter.

Example 2

The silica-based fine particles 2 in the above Synthesis Example 4 were mixed with the same polylactic acid under the same conditions as in Example 1 to obtain a composition. This composition was molded, and the bending strength and the elongation (bending strain) were measured, as in Example 1. The evaluation results are shown in Table 1.

Synthesis Example 5

Synthesis of Organic Silicon Compound 3

As an example of the organic silicon compound according to the present invention, a compound in which a group represented by the following chemical formula (B) corresponding to the first section, and a group represented by the following chemical formula (F) corresponding to the third section were bonded to alkoxyorganopolysiloxane represented by the following chemical formula (A), the propyl group portions of its propoxy groups being replaced, was synthesized. Me in the formulas represents a methyl group, Pr represents a propyl group, and Bu represents a butyl group.

[Formula 14]

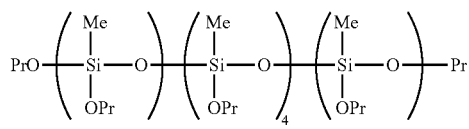

(A)

—CONH(CH$_2$)$_3$Si(OMe)$_3$ (B)

—(CH$_2$)$_5$CO(O(CH$_2$)$_5$CO)$_7$OBu (F)

The organic silicon compound 3 was obtained by preparing alkoxyorganopolysiloxane corresponding to the second section, introducing a resin-compatible chain into this polysiloxane, and then introducing an organic group containing an alkoxysilane group. Specifically, the organic silicon compound was synthesized in the following order of steps:

(a) propyloxymethyl silicone was synthesized,
(b) terminal hydroxy-modified polycaprolactone was synthesized,
(c) the propyloxymethyl silicone and the terminal hydroxy-modified polycaprolactone were bonded to form a silicone-bonded substance,
(d) a silanol group was formed in the propyloxymethyl silicone in the above bonded substance, and
(e) the silanol group of the propyloxymethyl silicone in the above bonded substance and isocyanatepropyltrimethoxysilane were bonded.

A description will be given below in this order of steps.

Step (a)

Linear propyloxymethyl silicone was prepared as in Synthesis Example 1.

Step (b)

As shown in the following reaction formula, s-caprolactone (PLACCE M manufactured by DAICEL CHEMICAL INDUSTRIES, LTD.) was ring-opening polymerized, using 1-butanol as an initiator, in the following manner, to synthesize terminal hydroxy-modified polycaprolactone.

69 g (600 mmol) of the s-caprolactone, 5.7 g (76 mmol) of 1-butanol, and 2.1×10$^{-3}$ g of tin octylate as a catalyst were added to a 200 ml eggplant flask and stirred under a nitrogen atmosphere at 150° C. for 15 hours. Then, the unreacted ε-caprolactone and the 1-butanol were removed by distillation by heating under reduced-pressure (150° C., 10 mmHg (1.33 kPa)). From $^1$H-NMR, an oligomer having a number average molecular weight of 1000 was confirmed. The yield was 95%.

[Formula 15]

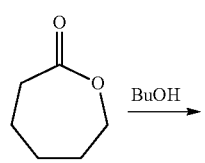 BuOH →

-continued

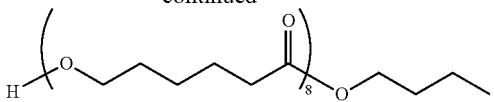

Step (c)

The above propyloxymethyl silicone and terminal hydroxy-modified polycaprolactone were bonded by a dealcoholization reaction between the propyloxy group and the hydroxyl group in the following manner.

5.6 g of the propyloxymethyl silicone, 7.0 g (7 mmol) of the terminal hydroxy-modified polycaprolactone, 6.7×10$^{-2}$ g (7 mmol) of methanesulfonic acid as a catalyst, and 20 ml of toluene were added to a 100 ml three-neck eggplant flask. The flask was equipped with a reduced-pressure distillation apparatus and a dropping funnel. The materials were stirred for 5 hours, while toluene was dropped at a speed of 1 ml per minute, and produced 1-propanol and the toluene were distilled off under a reduced pressure of 150 mmHg (20 kPa) at 60° C. Then, 5.5×10$^{-2}$ g (7 mmol) of pyridine was added to neutralize the methanesulfonic acid. The salt was removed by filtration, and then, the remaining 1-propanol and toluene were distilled off, using a rotary evaporator. From $^1$H-NMR, the reaction rate was 98%.

Step (d)

Part of the propyloxy groups of the above bonded substance were converted to a silanol group by hydrolysis in the following manner.

9.8 g of the above bonded substance, 1.8 g of an aqueous hydrochloric acid solution with its pH adjusted to 2.5, and 60 ml of acetone were added to a 200 ml Erlenmeyer flask and stirred in the air at 20° C. for 150 minutes. Then, 0.6 g of a 0.01 M aqueous sodium hydroxide solution was added to neutralize the hydrochloric acid. 50 g of magnesium sulfate (anhydrous) was added, and dehydration and drying were performed for 2 hours. Then, the salt and the magnesium sulfate were removed by filtration, and the acetone was distilled off, using a rotary evaporator. From $^1$H-NMR, the conversion rate to silanol group was calculated as 15% (on average, one silanol group was formed in one molecule). The silanol group was formed, while a condensation reaction due to the reaction between silanol groups was sufficiently suppressed.

Step (e)

The above bonded substance in which the silanol group was formed and isocyanatepropyltrimethoxysilane (SII6456.0 manufactured by AZmax Co.) were bonded by a reaction between the silanol group and the isocyanate group in the following manner.

8.2 g of the above bonded substance, 1.0 g (5.0 mmol) of the isocyanatepropyltrimethoxysilane, and 2.5×10$^{-3}$ g of tin octylate as a catalyst were added to a 50 ml eggplant flask and stirred under a nitrogen atmosphere at 20° C. for 48 hours. From $^1$H-NMR, the reaction rate was 86%.

The number average molecular weight of the obtained organic silicon compound was measured by GPC (gel permeation chromatography, "10A-VP" manufactured by SHIMADZU CORPORATION, columns: two GPC-80MC and one GPC-8025C, developing solvent: chloroform, standard sample: polystyrene) to be 2300.

Synthesis Example 6

Manufacture of Silica-Based Fine Particles 3

Silica-based fine particles were manufactured from the above organic silicon compound 3 by the following two-stage step:

(1) the sol-gel reaction of the methoxy groups of the first sections (the formation of a core), and
(2) the sol-gel reaction of the propyloxy groups of the second sections (the formation of an intermediate region, and as a result, the formation of a surface layer derived from the third sections).

A description will be given below in this order of steps.

Step (1)

8.7 g of the above organic silicon compound 3, 16 g of 29% ammonia water, and 100 ml of acetone were added to a 200 ml eggplant flask and stirred in the air at 20° C. for 24 hours. Then, produced methanol, the water, the ammonia, and the acetone were distilled off, using a rotary evaporator. From $^1$H-NMR, it was confirmed that the reaction rate of the methoxy groups was 85%, and the reaction of the propyloxy groups hardly proceeded (5% or less).

Step (2)

6.0 g of the condensation substance obtained in the step (1), 80 g of 29% ammonia water, and 500 ml of acetone were added to a 1 L Erlenmeyer flask and stirred in the air at 20° C. for 36 hours. Then, produced 1-propanol, the ammonia water, and the acetone were distilled off, using a rotary evaporator. From $^1$H-NMR, the reaction rate of the propyloxy groups was 82%.

From the observation of the obtained silica-based fine particles by an STEM (scanning transmission electron microscope, HD-2300 manufactured by Hitachi High-Technologies Corporation), the average particle diameter of the silica-based fine particles was about 30 nm. In this STEM observation, the diameters of randomly selected 10 fine particles were measured, and their average value was calculated as the average particle diameter.

Example 3

The silica-based fine particles 3 in the above Synthesis Example 6 were mixed with the same polylactic acid under the same conditions as in Example 1 to obtain a composition. This composition was molded, and the bending strength and the elongation (bending strain) were measured, as in Example 1. The evaluation results are shown in Table 1.

Synthesis Example 7

Synthesis of Organic Silicon Compound 4

As an example of the organic silicon compound according to the present invention, a compound in which a group represented by the following chemical formula (G) corresponding to the first section, and a group represented by the following chemical formula (C) corresponding to the third section were bonded to alkoxyorganopolysiloxane represented by the following chemical formula (A), the propyl group portions of its propoxy groups being replaced, was synthesized. Me in the formulas represents a methyl group, Pr represents a propyl group, and Bu represents a butyl group.

[Formula 16]

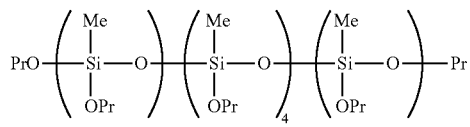

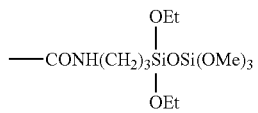

(G)

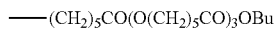

——(CH$_2$)$_5$CO(O(CH$_2$)$_5$CO)$_3$OBu    (C)

The organic silicon compound 4 was obtained by preparing alkoxyorganopolysiloxane corresponding to the second section, introducing a resin-compatible chain into this polysiloxane, and then introducing an alkoxysilane compound having two alkoxy groups. Specifically, the organic silicon compound was synthesized in the following order of steps:

(a) propyloxymethyl silicone was synthesized,
(b) terminal hydroxy-modified polycaprolactone was synthesized,
(c) the propyloxymethyl silicone and the terminal hydroxy-modified polycaprolactone were bonded to form a silicone-bonded substance,
(d) a silanol group was formed in the propyloxymethyl silicone in the above bonded substance,
(e) isocyanatepropyltriethoxysilane and tetramethoxysilane were bonded to form a silane-bonded substance, and
(f) the reaction of the silanol group formed in the step (d), in the above silicone-bonded substance, with the isocyanate group of the silane-bonded substance synthesized in the step (e).

A description will be given below in this order of steps.

Steps (a) to (d)

The steps (a) to (d) were performed as in Synthesis Example 1.

Step (e)

Partially hydrolyzed isocyanatepropyltriethoxysilane and tetramethoxysilane (LS-540 manufactured by Shin-Etsu Chemical Co., Ltd.) were bonded by a reaction between the silanol group and the methoxy group in the following manner to obtain a silane-bonded substance.

The partial hydrolysis reaction of isocyanatepropyltriethoxysilane was performed in the following manner. 4.9 g (20 mmol) of isocyanatepropyltriethoxysilane, 0.4 g of an aqueous hydrochloric acid solution adjusted to pH 1.7, and 3 ml of tetrahydrofuran were added to a 50 ml eggplant flask and stirred in the air at 20° C. for 30 minutes. Then, 0.2 g of a 0.01 M aqueous sodium hydroxide solution was added to neutralize the hydrochloric acid. 50 g of magnesium sulfate (anhydrous) was added, and dehydration and drying were performed for 2 hours. Then, the salt and the magnesium sulfate were removed by filtration, and produced ethanol and the tetrahydrofuran were distilled off, using a rotary evaporator. From $^1$H-NMR, the conversion rate from ethoxy group to silanol group was calculated as 30% (on average, one silanol group was formed in one molecule). The silanol group was formed, while a condensation reaction due to the reaction between silanol groups was sufficiently suppressed.

Next, 2.4 g of the above partially hydrolyzed compound, 1.5 g (10 mmol) of tetramethoxysilane, and 9.6×10$^{-2}$ g (10 mmol) of methanesulfonic acid were added to a 50 ml eggplant flask and stirred under a nitrogen atmosphere at 60° C. for 3 hours. Then, 7.9×10$^{-2}$ g (10 mmol) of pyridine was added, and the salt was removed by filtration. The unreacted tetramethoxysilane was distilled off, using a rotary evaporator. From $^1$H-NMR, the reaction rate was 88%.

Step (f)

The silane-bonded substance obtained in the step (e) and the silicone-bonded substance obtained in the steps (c) and (d) were bonded by a reaction between the isocyanate group of the silane-bonded substance and the silanol group of the silicone-bonded substance in the following manner.

2.0 g of the silane-bonded substance obtained in the step (e), 7.8 g of the silicone-bonded substance obtained in the steps (c) and (d), and $2.3 \times 10^{-3}$ g of tin octylate as a catalyst were added to a 50 ml eggplant flask and stirred under a nitrogen atmosphere at 20° C. for 24 hours. From $^1$H-NMR, the reaction rate was 80%.

The number average molecular weight of the obtained organic silicon compound was measured by GPC (gel permeation chromatography, "10A-VP" manufactured by SHIMADZU CORPORATION, columns: two GPC-80MC and one GPC-8025C, developing solvent: chloroform, standard sample: polystyrene) to be 2000.

Synthesis Example 8

Manufacture of Silica-Based Fine Particles 4

Silica-based fine particles were manufactured from the above organic silicon compound 4 by the following two-stage step:
(1) the sol-gel reaction of the methoxy groups and the ethoxy groups of the first sections (the formation of a core), and
(2) the sol-gel reaction of the propyloxy groups of the second sections (the formation of an intermediate region, and as a result, the formation of a surface layer derived from the third sections).

A description will be given below in this order of steps.
Step (1)
19 g of the above organic silicon compound, 18 g (1 mol) of pure water, 32 g of 29% ammonia water, and 60 ml of acetone were added to a 500 ml eggplant flask and stirred in the air at 20° C. for 12 hours. Then, produced methanol and ethanol, the water, the ammonia, and the acetone were distilled off, using a rotary evaporator. From $^1$H-NMR, it was confirmed that the reaction rate of the methoxy groups and the ethoxy groups was 85%, and the reaction of the propyloxy groups hardly proceeded (5% or less).
Step (2)
6.0 g of the condensation substance obtained in the step (1), 80 g of 29% ammonia water, and 500 ml of acetone were added to a 1 L eggplant flask and stirred in the air at 20° C. for 24 hours. Then, produced 1-propanol, the ammonia water, and the acetone were distilled off, using a rotary evaporator. From $^1$H-NMR, it was confirmed that the reaction rate of the propyloxy groups of the second section of the silicon compound was 82%.

From the observation of the obtained silica-based fine particles by an STEM (scanning transmission electron microscope, HD-2300 manufactured by Hitachi High-Technologies Corporation), the average particle diameter of the silica-based fine particles was about 30 nm. In this STEM observation, the diameters of randomly selected 10 fine particles were measured, and their average value was calculated as the average particle diameter.

Example 4

The silica-based fine particles 4 in the above Synthesis Example 8 were mixed with the same polylactic acid under the same conditions as in Example 1 to obtain a composition. This composition was molded, and the bending strength and the elongation (bending strain) were measured, as in Example 1. The evaluation results are shown in Table 1.

Synthesis Example 9

Synthesis of Organic Silicon Compound 5

As an example of the organic silicon compound according to the present invention, a compound in which a group represented by the following chemical formula (H) corresponding to the first section, and a group represented by the following chemical formula (F) corresponding to the third section were bonded to alkoxyorganopolysiloxane represented by the following chemical formula (A), the propyl group portions of its propoxy groups being replaced, was synthesized. Me in the formulas represents a methyl group, Pr represents a propyl group, and Bu represents a butyl group.

[Formula 17]

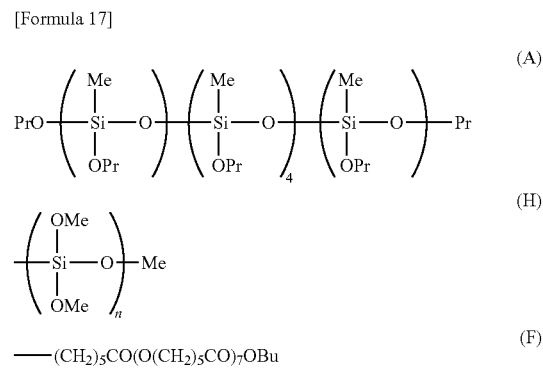

The organic silicon compound 5 was obtained by preparing alkoxyorganopolysiloxane corresponding to the second section, introducing a resin-compatible chain into this polysiloxane, and then introducing methoxy silicone corresponding to the first section. Specifically, the organic silicon compound was synthesized in the following order of steps:
(a) propyloxymethyl silicone was synthesized,
(b) terminal hydroxy-modified polycaprolactone was synthesized,
(c) the propyloxymethyl silicone and the terminal hydroxy-modified polycaprolactone were bonded to form a silicone-bonded substance,
(d) a silanol group was formed in the propyloxymethyl silicone in the above bonded substance, and
(e) the silanol group of the propyloxymethyl silicone in the above bonded substance and methoxy silicone were bonded.

A description will be given below in this order of steps.
Step (a)
Linear propyloxymethyl silicone was prepared as in Synthesis Example 1.
Step (b)
Terminal hydroxy-modified polycaprolactone was prepared as in Synthesis Example 5.
Step (c)
The above propyloxymethyl silicone and terminal hydroxy-modified polycaprolactone were bonded by a dealcoholization reaction between the propyloxy group and the hydroxyl group in the following manner.
5.6 g of the propyloxymethyl silicone, 7.0 g (7 mmol) of the terminal hydroxy-modified polycaprolactone, $6.7 \times 10^{-2}$ g (7 mmol) of methanesulfonic acid as a catalyst, and 20 ml of toluene were added to a 100 ml three-neck eggplant flask. The flask was equipped with a reduced-pressure distillation apparatus and a dropping funnel. The materials were stirred for 5 hours, while toluene was dropped at a speed of 1 ml per minute, and produced 1-propanol and the toluene were distilled off under a reduced pressure of 150 mmHg (20 kPa) at 60° C. Then, $5.5 \times 10^{-2}$ g (7 mmol) of pyridine was added to neutralize the methanesulfonic acid. The salt was removed by filtration, and then, the remaining 1-propanol and toluene were distilled off, using a rotary evaporator. From $^1$H-NMR, the reaction rate was 98%.

Step (d)

Part of the propyloxy groups of the above bonded substance were converted to a silanol group by hydrolysis in the following manner.

9.8 g of the above bonded substance, 1.8 g of an aqueous hydrochloric acid solution with its pH adjusted to 2.5, and 60 ml of acetone were added to a 200 ml Erlenmeyer flask and stirred in the air at 20° C. for 150 minutes. Then, 0.6 g of a 0.01 M aqueous sodium hydroxide solution was added to neutralize the hydrochloric acid. 50 g of magnesium sulfate (anhydrous) was added, and dehydration and drying were performed for 2 hours. Then, the salt and the magnesium sulfate were removed by filtration, and the acetone was distilled off, using a rotary evaporator. From $^1$H-NMR, the conversion rate to silanol group was calculated as 15% (on average, one silanol group was formed in one molecule). The silanol group was formed, while a condensation reaction due to the reaction between silanol groups was sufficiently suppressed.

Step (e)

The above bonded substance in which the silanol group was formed and methoxy silicone (X-40-2308 manufactured by Shin-Etsu Chemical Co., Ltd.) were bonded by a dealcoholization reaction between the silanol group and the methoxy group in the following manner.

8.2 g of the above bonded substance, 2.8 g of the methoxy silicone, $5.4 \times 10^{-1}$ g (56 mmol) of methanesulfonic acid as a catalyst, and 20 ml of tetrahydrofuran were added to a 100 ml three-neck eggplant flask. The materials were stirred for 3 hours, while tetrahydrofuran was dropped at a speed of 1 ml per minute, and produced methanol and the tetrahydrofuran were distilled off under nitrogen at 70° C. Then, $4.4 \times 10^{-1}$ g (56 mmol) of pyridine was added to neutralize the methanesulfonic acid. The salt was removed by filtration, and then, the remaining methanol and tetrahydrofuran were distilled off, using a rotary evaporator. From $^1$H-NMR, the reaction rate was 98%.

The number average molecular weight of the obtained organic silicon compound was measured by GPC (gel permeation chromatography, "10A-VP" manufactured by SHIMADZU CORPORATION, columns: two GPC-80MC and one GPC-8025C, developing solvent: chloroform, standard sample: polystyrene) to be 2500.

Synthesis Example 10

Manufacture of Silica-Based Fine Particles 5

Silica-based fine particles were manufactured from the above organic silicon compound 5 by the following two-stage step:

(1) the sol-gel reaction of the methoxy groups of the first sections (the formation of a core), and (2) the sol-gel reaction of the propyloxy groups of the second sections (the formation of an intermediate region, and as a result, the formation of a surface layer derived from the third sections).

A description will be given below in this order of steps.

Step (1)

8.7 g of the above organic silicon compound 5, 16 g of 29% ammonia water, and 100 ml of acetone were added to a 200 ml eggplant flask and stirred in the air at 20° C. for 24 hours. Then, produced methanol, the water, the ammonia, and the acetone were distilled off, using a rotary evaporator. From $^1$H-NMR, it was confirmed that the reaction rate of the methoxy groups was 85%, and the reaction of the propyloxy groups hardly proceeded (5% or less).

Step (2)

6.0 g of the condensation substance obtained in the step (1), 80 g of 29% ammonia water, and 500 ml of acetone were added to a 1 L Erlenmeyer flask and stirred in the air at 20° C. for 36 hours. Then, produced 1-propanol, the ammonia water, and the acetone were distilled off, using a rotary evaporator. From $^1$H-NMR, the reaction rate of the propyloxy groups was 78%.

From the observation of the obtained silica-based fine particles by an STEM (scanning transmission electron microscope, HD-2300 manufactured by Hitachi High-Technologies Corporation), the average particle diameter of the silica-based fine particles was about 20 nm. In this STEM observation, the diameters of randomly selected 10 fine particles were measured, and their average value was calculated as the average particle diameter.

Example 5

The silica-based fine particles 5 in the above Synthesis Example 10 were mixed with the same polylactic acid under the same conditions as in Example 1 to obtain a composition. This composition was molded, and the bending strength and the elongation (bending strain) were measured, as in Example 1. The evaluation results are shown in Table 1.

Synthesis Example 11

Synthesis of Organic Silicon Compound 6

As an example of the organic silicon compound according to the present invention, a compound in which a group represented by the following chemical formula (E) corresponding to the first section, and a group represented by the following chemical formula (J) corresponding to the third section were bonded to alkoxyorganopolysiloxane represented by the following chemical formula (A), the propyl group portions of its propyloxy groups being replaced, was synthesized. Me in the formulas represents a methyl group, and Et represents an ethyl group.

[Formula 18]

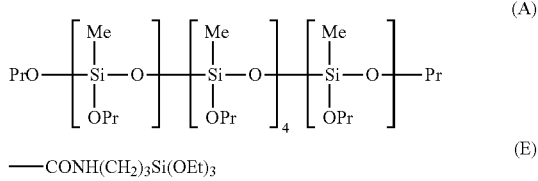

-continued

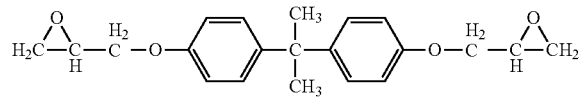
(J)

The organic silicon compound 6 was obtained by preparing alkoxyorganopolysiloxane corresponding to the second section, introducing an organic group containing an alkoxysilane group into this polysiloxane, and then introducing an organic group containing a reactive functional group. Specifically, the organic silicon compound was synthesized in the following order of steps:
(a) propyloxymethyl silicone was synthesized,
(b) silanol groups were formed in the propyloxymethyl silicone (on average, two silanol groups were formed in one molecule),
(c) part of the silanol groups of the propyloxymethyl silicone and isocyanatepropyltriethoxysilane were bonded to form a silicone-triethoxysilane-bonded substance, and
(d) the silanol group of the propyloxymethyl silicone in the above silicone-triethoxysilane-bonded substance and a bisphenol A type epoxy compound were bonded.

A description will be given below in this order of steps.

Step (a)

Linear propyloxymethyl silicone was prepared as in Synthesis Example 1.

Step (b)

Part of the propyloxy groups of the propyloxymethyl silicone were converted to silanol groups by hydrolysis in the following manner to prepare silanol-modified propyloxymethyl silicone.

14 g of the propyloxymethyl silicone, 6.0 g of an aqueous hydrochloric acid solution with its pH adjusted to 2.5, and 120 ml of acetone were added to a 200 ml Erlenmeyer flask and stirred in the air at 20° C. for 1 hour. Then, 1.6 g of a 0.01 M aqueous sodium hydroxide solution was added to neutralize the hydrochloric acid. 50 g of magnesium sulfate (anhydrous) was added, and dehydration and drying were performed for 2 hours. Then, the salt and the magnesium sulfate were removed by filtration, and the acetone was distilled off, using a rotary evaporator. From $^1$H-NMR, the conversion rate to silanol groups was calculated as 28% (on average, two silanol groups were formed in one molecule). The silanol groups were formed, while a condensation reaction due to the reaction between silanol groups was sufficiently suppressed.

Step (c)

The silanol-modified propyloxymethyl silicone obtained in the above step (b) and isocyanatepropyltriethoxysilane (LS-3415 manufactured by Shin-Etsu Chemical Co., Ltd.) were bonded by a reaction between part of the formed silanol groups and the isocyanate group in the following manner (½ equivalent of isocyanate groups with respect to silanol groups).

11 g of the silanol-modified propyloxymethyl silicone, 1.9 g (7.5 mmol) of the isocyanatepropyltriethoxysilane, and 3.3×10 g of tin octylate as a catalyst were added to a 50 ml eggplant flask and stirred under a nitrogen atmosphere at 20° C. for 48 hours. From $^1$H-NMR, the reaction rate of the isocyanate groups was 95%.

Step (d)

The silicone-triethoxysilane-bonded substance obtained in the above step (c) and a bisphenol A type diglycidyl ether represented by the chemical formula (J) (D3415 manufactured by aldrich) were bonded by a reaction between the remaining silanol group and the epoxy group in the following manner (2 equivalents of epoxy groups with respect to silanol groups).

10 g of the above bonded substance, 9 g of the bisphenol A type diglycidyl ether, and 100 ml of toluene were added to a 200 ml eggplant flask, and stirred under a nitrogen atmosphere at 100° C. for 3 hours, while water produced during reaction was extracted by Soxhlet extraction. From $^1$H-NMR, the reaction rate of the epoxy groups was 45%, and the elimination of the silanol groups was confirmed.

The number average molecular weight of the obtained organic silicon compound was measured by GPC (gel permeation chromatography, "10A-VP" manufactured by SHIMADZU CORPORATION, columns: two GPC-80MC and one GPC-8025C, developing solvent: chloroform, standard sample: polystyrene) to be 2000.

Synthesis Example 12

Manufacture of Silica-Based Fine Particles 6

Silica-based fine particles 6 were manufactured from the organic silicon compound 6 in the above Synthesis Example 11 by the following two-stage step:
(1) the sol-gel reaction of the ethoxy groups of the first sections (the formation of a core), and
(2) the sol-gel reaction of the propyloxy groups of the second sections (the formation of an intermediate region, and as a result, the formation of a surface layer derived from the third sections).

A description will be given below in this order of steps.

Step (1)

10 g of the above organic silicon compound 6, 9.0 g (0.5 mol) of pure water, and 30 ml of acetone were added to a 200 ml eggplant flask and stirred in the air at 20° C. for 48 hours. Then, produced ethanol, the water, and the acetone were distilled off, using a rotary evaporator. From $^1$H-NMR, it was confirmed that the reaction rate of the ethoxy groups was 87%, and the reaction of the propyloxy groups and the epoxy groups hardly proceeded (5% or less).

Step (2)

6.0 g of the condensation substance obtained in the step (1), 27 g (1.5 mol) of pure water, and 500 ml of acetone were added to a 1 L Erlenmeyer flask and stirred in the air at 20° C. for 48 hours. Then, produced 1-propanol, the water, and the acetone were distilled off, using a rotary evaporator. From $^1$H-NMR, the reaction rate of the propyloxy groups was 83%.

From the observation of the obtained silica-based fine particles by an STEM (scanning transmission electron microscope, HD-2300 manufactured by Hitachi High-Technologies Corporation), the average particle diameter of the silica-based fine particles was about 35 nm. In this STEM observation, the diameters of randomly selected 10 fine particles were measured, and their average value was calculated as the average particle diameter.

Example 6

100 g of a bisphenol A type epoxy resin (AER260 manufactured by Asahi Kasei Epoxy Co., Ltd.) was added to and mixed in 500 ml of acetone containing 5.0 g of the silica-based fine particles 6 in the above Synthesis Example 12. Then, while the mixture was heated at 50° C., the pressure was reduced by an aspirator to remove the solvent. Further, 11 g of diethylenetriamine as a curing agent was added and mixed to obtain an epoxy resin composition containing 5% by weight of the silica-based fine particles.

This resin composition was poured into a mold on a hot plate, allowed to stand at room temperature for 48 hours, and heated at 120° C. for 3 hours and further at 150° C. for 3 hours for curing to fabricate test pieces with a thickness of 2 mm, a length of 40 mm, and a width of 25 mm. Then, the bending strength and elongation (bending strain) of the test pieces were measured by the same method as in Example 1. The evaluation results are shown in Table 1.

Synthesis Example 13

Synthesis of Organic Silicon Compound 7

As an example of the organic silicon compound according to the present invention, a compound in which a group represented by the following chemical formula (E) corresponding to the first section, and a group represented by the following chemical formula (J) corresponding to the third section were bonded to alkoxyorganopolysiloxane represented by the following chemical formula (D), the ethyl group portions of its ethoxy groups being replaced, was synthesized. Me in the formulas represents a methyl group, and Et represents an ethyl group.

[Formula 19]

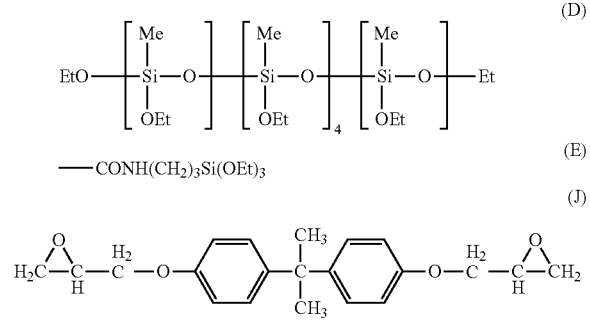

—CONH(CH$_2$)$_3$Si(OEt)$_3$  (E)

(J)

The organic silicon compound 7 was obtained by preparing alkoxyorganopolysiloxane corresponding to the second section, introducing an organic group containing an alkoxysilane group into this polysiloxane, and then introducing an organic group containing a reactive functional group. Specifically, the organic silicon compound was synthesized in the following order of steps:
(a) ethoxymethyl silicone was synthesized,
(b) silanol groups were formed in the ethoxymethyl silicone (on average, two silanol groups were formed in one molecule),
(c) part of the silanol groups of the ethoxymethyl silicone and isocyanatepropyltriethoxysilane were bonded to form a silicone-triethoxysilane-bonded substance, and
(d) the silanol group of the ethoxymethyl silicone in the above silicone-triethoxysilane-bonded substance and a bisphenol A type epoxy compound were bonded.

A description will be given below in this order of steps.
Step (a)
Linear ethoxymethyl silicone was prepared as in Synthesis Example 3.
Step (b)
Part of the ethoxy groups of the ethoxymethyl silicone were converted to silanol groups by hydrolysis in the following manner to prepare silanol-modified ethoxymethyl silicone.

14 g of the ethoxymethyl silicone, 4.0 g of an aqueous hydrochloric acid solution with its pH adjusted to 2.5, and 100 ml of acetone were added to a 200 ml Erlenmeyer flask and stirred in the air at 20° C. for 1 hour. Then, 0.8 g of a 0.01 M aqueous sodium hydroxide solution was added to neutralize the hydrochloric acid. 50 g of magnesium sulfate (anhydrous) was added, and dehydration and drying were performed for 2 hours. Then, the salt and the magnesium sulfate were removed by filtration, and the acetone was distilled off, using a rotary evaporator. From $^1$H-NMR, the conversion rate to silanol groups was calculated as 28% (on average, two silanol groups were formed in one molecule). The silanol groups were formed, while a condensation reaction due to the reaction between the silanol groups was sufficiently suppressed.
Step (c)
The silanol-modified ethoxymethyl silicone obtained in the above step (b) and isocyanatepropyltriethoxysilane (LS-3415 manufactured by Shin-Etsu Chemical Co., Ltd.) were bonded by a reaction between part of the formed silanol groups and the isocyanate group in the following manner (½ equivalent of isocyanate groups with respect to silanol groups).

12 g of the silanol-modified ethoxymethyl silicone, 1.9 g (7.5 mmol) of the isocyanatepropyltriethoxysilane, and 3.6× $10^{-3}$ g of tin octylate as a catalyst were added to a 50 ml eggplant flask and stirred under a nitrogen atmosphere at 20° C. for 48 hours. From $^1$H-NMR, the reaction rate was 85%.
Step (d)
The silicone-triethoxysilane-bonded substance obtained in the above step (c) and a bisphenol A type diglycidyl ether represented by the chemical formula (J) (D3415 manufactured by aldrich) were bonded by a reaction between the remaining silanol group and the epoxy group in the following manner (2 equivalents of epoxy groups with respect to silanol groups).

10 g of the above bonded substance, 9 g of the bisphenol A type diglycidyl ether, and 100 ml of toluene were added to a 200 ml eggplant flask, and stirred under a nitrogen atmosphere at 100° C. for 3 hours, while water produced during reaction was extracted by Soxhlet extraction. From $^1$H-NMR, the reaction rate of the epoxy groups was 45%, and the elimination of the silanol groups was confirmed.

The number average molecular weight of the obtained organic silicon compound was measured by GPC (gel permeation chromatography, "10A-VP" manufactured by SHIMADZU CORPORATION, columns: two GPC-80MC and one GPC-8025C, developing solvent: chloroform, standard sample: polystyrene) to be 2000.

Synthesis Example 14

Manufacture of Silica-Based Fine Particles 7

Silica-based fine particles 7 were manufactured from the organic silicon compound 7 in the above Synthesis Example 13 by the following two-stage step:
(1) the sol-gel reaction of the groups of the first sections (the formation of a core), and
(2) the sol-gel reaction of the ethoxy groups of the second sections (the formation of an intermediate region, and as a result, the formation of a surface layer derived from the third sections).

A description will be given below in this order of steps.
Step (1)
10 g of the above organic silicon compound, 9.0 g (0.5 mol) of pure water, and 50 ml of acetone were added to a 200 ml eggplant flask and stirred in the air at 20° C. for 24 hours.

Step (2)

1.0 g of 29% ammonia water and 200 ml of acetone were added to the solution obtained in the step (1) and stirred in the air at 20° C. for 24 hours. Then, produced ethanol, the ammonia water, and the acetone were distilled off, using a rotary evaporator. From $^1$H-NMR, it was confirmed that the reaction rate of the ethoxy groups of the silicon compound was 83%.

From the observation of the obtained silica-based fine particles by an STEM (scanning transmission electron microscope, HD-2300 manufactured by Hitachi High-Technologies Corporation), the average particle diameter of the silica-based fine particles was about 40 nm. In this STEM observation, the diameters of randomly selected 10 fine particles were measured, and their average value was calculated as the average particle diameter.

Example 7

100 g of a bisphenol A type epoxy resin (AER260 manufactured by Asahi Kasei Epoxy Co., Ltd.) was added to and mixed in 500 ml of acetone containing 5.0 g of the silica-based fine particles 7 in the above Synthesis Example 14. Then, while the mixture was heated at 50° C., the pressure was reduced by an aspirator to remove the solvent. Further, the resulting material was heated to 80° C., and then, 11 g of diethylenetriamine as a curing agent was added and mixed to obtain an epoxy resin composition containing 5% by weight of the silica-based fine particles.

This resin composition was poured into a mold on a hot plate, heated at 85° C. for 2 hours, and then cured at 150° C. for 2 hours to fabricate test pieces with a thickness of 2 mm, a length of 40 mm, and a width of 25 mm. Then, the bending strength and elongation (bending strain) of the test pieces were measured by the same method as in Example 1. The evaluation results are shown in Table 1.

Example 8

The silica-based fine particles 1 in Synthesis Example 2 were mixed with the same epoxy resin and curing agent under the same conditions as in Example 6 to obtain a composition. This composition was molded, and the bending strength and the elongation (bending strain) were measured, as in Example 6. The evaluation results are shown in Table 1.

Example 9

100 g of cellulose acetate (L-40 manufactured by DAICEL CHEMICAL INDUSTRIES, LTD., number average molecular weight: $4.4 \times 10^4$) as a cellulosic resin was added to and mixed in 500 ml of chloroform containing 6.5 g of the silica-based fine particles 1 in Synthesis Example 2 While the mixture was heated at 50° C., the pressure was reduced by an aspirator to remove the solvent. Then, 30 g of triethyl citrate (CITROFLEX2 manufactured by Morflex Inc.) as a plasticizer was added to obtain a cellulose acetate resin composition containing 5% by weight of the silica-based fine particles.

This resin composition was heated and melted on a hot plate at 220° C. and poured into a mold to fabricate test pieces with a thickness of 2 mm, a length of 40 mm, and a width of 25 mm. Then, the bending strength and elongation (bending strain) of the test pieces were measured by the same method as in Example 1. The evaluation results are shown in Table 1.

Example 10

The silica-based fine particles 3 in Synthesis Example 6 were mixed with the same cellulose acetate and plasticizer under the same conditions as in Example 9 to obtain a composition. This composition was molded, and the bending strength and the elongation (bending strain) were measured, as in Example 9. The evaluation results are shown in Table 1.

Comparative Example 1

The polylactic acid used in Example 1 alone was evaluated as in Example 1. The evaluation results are shown in Table 2.

Comparative Example 2

5 g of silica fine particles having a nanosize diameter (average particle diameter: 12 nm) (AEROJIL®200 manufactured by NIPPON AEROSIL CO., LTD.) were dispersed in 500 ml of chloroform, and 100 g of polylactic acid was added to and mixed with the dispersion. Then, as in the Examples, while the mixture was heated at 50° C., the pressure was reduced by an aspirator to remove the solvent to obtain a resin composition containing 5% by weight of the silica fine particles. This resin composition was evaluated as in Example 1. The evaluation results are shown in Table 2.

Comparative Example 3

For a bonded substance prepared as in Synthesis Example 1, which is obtained by bonding propyloxymethyl silicone and terminal hydroxy-modified polycaprolactone, the propyloxy groups were condensed by a sol-gel reaction in the following manner to obtain fine particles.

6.0 g of the above bonded substance, 40 g of 29% ammonia water, and 100 ml of acetone were added to a 300 ml eggplant flask and stirred in the air at 20° C. for 24 hours. Then, produced 1-propanol, the ammonia water, and the acetone were distilled off, using a rotary evaporator. From $^1$H-NMR, it was confirmed that the reaction rate of the propyloxy groups was 75%.

From the observation of the obtained fine particles by an STEM (scanning transmission electron microscope, HD-2300 manufactured by Hitachi High-Technologies Corporation), the average particle diameter of the fine particles was about 500 nm. In this STEM observation, the diameters of randomly selected 10 fine particles were measured, and their average value was calculated as the average particle diameter.

5 g of the fine particles were dispersed in 500 ml of chloroform, and 100 g of polylactic acid was added to and mixed with the dispersion. Then, while the mixture was heated at 50° C., the pressure was reduced by an aspirator to remove the solvent to obtain a resin composition containing 5% by weight of the above fine particles. This resin composition was evaluated as in Example 1. The evaluation results are shown in Table 2.

Comparative Example 4

Propyloxymethyl silicone prepared as in Synthesis Example 1 was reacted with isocyanatepropyltrimethoxysilane to make a bonded substance of these. Using this bonded substance, the propyloxy groups were condensed by a sol-gel reaction to obtain fine particles.

In the above manufacturing process, part of the propyloxy groups of the above propyloxymethyl silicone were converted to a silanol group by hydrolysis in the following manner, and the silanol group was reacted with the isocyanate group in the isocyanatepropyltrimethoxysilane to obtain the bonded substance.

23 g of the propyloxymethyl silicone, 5.4 g of an aqueous hydrochloric acid solution with its pH adjusted to 2.5, and 180 ml of acetone were added to a 300 ml Erlenmeyer flask and stirred in the air at 20° C. for 150 minutes. Then, 1.8 g of a 0.01 M aqueous sodium hydroxide solution was added to neutralize the hydrochloric acid. 50 g of magnesium sulfate (anhydrous) was added, and dehydration and drying were performed for 2 hours. Then, the salt and the magnesium sulfate were removed by filtration, and the acetone was distilled off, using a rotary evaporator. From $^1$H-NMR, the conversion rate to silanol group was calculated as 15% (on average, one silanol group was formed in one molecule).

Next, 15 g of the above propyloxymethyl silicone in which silanol group was formed, 4.0 g (20 mmol) of isocyanatepropyltrimethoxysilane, and $4.5 \times 10^{-3}$ g of tin octylate as a catalyst were added to a 20 ml eggplant flask and stirred under a nitrogen atmosphere at 20° C. for 16 hours. From $^1$H-NMR, the reaction rate was 90%.

Using the bonded substance obtained in the above manner, fine particles were formed in the following manner.

10 g of the above bonded substance, 9 g (0.5 mol) of pure water, 16 g of 29% ammonia water, and 100 ml of acetone were added to a 500 ml eggplant flask and stirred in the air at 20° C. for 12 hours. Then, produced methanol, the water, the ammonia, and the acetone were distilled off, using a rotary evaporator. From $^1$H-NMR, it was confirmed that the reaction rate of the methoxy groups was 78%, and the reaction of the propyloxy groups hardly proceeded.

Next, 8.0 g of the condensation substance obtained in the above step, 60 g of 29% ammonia water, and 600 ml of acetone were added to a 500 ml eggplant flask and stirred in the air at 20° C. for 24 hours. Then, produced 1-propanol, the ammonia water, and the acetone were distilled off, using a rotary evaporator. From $^1$H-NMR, it was confirmed that the reaction rate of the propyloxy groups of the condensate was 89%.

From the observation of the obtained fine particles by an STEM (scanning transmission electron microscope, HD-2300 manufactured by Hitachi High-Technologies Corporation), the average particle diameter of the fine particles was about 15 nm. In this STEM observation, the diameters of randomly selected 10 fine particles were measured, and their average value was calculated as the average particle diameter.

5 g of the fine particles were dispersed in 500 ml of chloroform, and 100 g of polylactic acid was added to and mixed with the dispersion. Then, while the mixture was heated at 50° C., the pressure was reduced by an aspirator to remove the solvent to obtain a resin composition containing 5% by weight of the above fine particles. This resin composition was evaluated as in Example 1. The evaluation results are shown in Table 2.

Comparative Example 5

Terminal hydroxy-modified polycaprolactone prepared as in Synthesis Example 1 was reacted with isocyanatepropyltrimethoxysilane to make a bonded substance of these. Using this bonded substance, the methoxy groups were condensed by a sol-gel reaction to obtain fine particles. Specifically, this process was performed as follows.

5.5 g (10 mmol) of the terminal hydroxy-modified polycaprolactone, 2.0 g (10 mmol) of isocyanatepropyltrimethoxysilane, and $1.8 \times 10^{-3}$ g of tin octylate as a catalyst were added to a 20 ml eggplant flask and stirred under a nitrogen atmosphere at 20° C. for 24 hours. From $^1$H-NMR, the reaction rate was 90%.

Next, 6.0 g of the compound obtained by the above step, 5.4 g (0.3 mol) of pure water, 16 g of 29% ammonia water, and 50 ml of acetone were added to a 500 ml eggplant flask and stirred in the air at 20° C. for 24 hours. Then, produced methanol, the water, the ammonia, and the acetone were distilled off, using a rotary evaporator. From $^1$H-NMR, the reaction rate of the methoxy groups was 85%.

From the observation of the obtained fine particles by an STEM (scanning transmission electron microscope, HD-2300 manufactured by Hitachi High-Technologies Corporation), the average particle diameter of the fine particles was about 10 nm. In this STEM observation, the diameters of randomly selected 10 fine particles were measured, and their average value was calculated as the average particle diameter.

5 g of the fine particles were dispersed in 500 ml of chloroform, and 100 g of polylactic acid was added to and mixed with the dispersion. Then, while the mixture was heated at 50° C., the pressure was reduced by an aspirator to remove the solvent to obtain a resin composition containing 5% by weight of the above fine particles. This resin composition was evaluated as in Example 1. The evaluation results are shown in Table 2.

Comparative Example 6

11 g of diethylenetriamine as a curing agent was added to and mixed with 100 g of the epoxy resin used in Example 6 to obtain a resin composition. This resin composition was evaluated as in Example 6. The evaluation results are shown in Table 2.

Comparative Example 7

30 g of triethyl citrate as a plasticizer was added to and mixed with 100 g of the cellulose acetate used in Example 9 to obtain a resin composition. This resin composition was evaluated as in Example 9. The evaluation results are shown in Table 2.

TABLE 1

|  | Bending strength (maximum stress) (MPa) | Elongation (at maximum stress) (%) |
|---|---|---|
| Example 1 | 100 | 10 (No break) |
| Example 2 | 95 | 10 (No break) |
| Example 3 | 110 | 7 (Break at maximum stress) |
| Example 4 | 106 | 10 (No break) |
| Example 5 | 114 | 7 (Break at maximum stress) |
| Example 6 | 112 | 10 (No break) |
| Example 7 | 115 | 10 (Break at maximum stress) |
| Example 8 | 105 | 9 (Break at maximum stress) |
| Example 9 | 91 | 10 (Break at maximum stress) |
| Example 10 | 90 | 8 (Break at maximum stress) |

TABLE 2

|  | Bending strength (maximum stress) (MPa) | Elongation (at maximum stress) (%) |
|---|---|---|
| Comparative Example 1 | 90 | 3 (Break at maximum stress) |
| Comparative Example 2 | 70 | 2 (Break at maximum stress) |
| Comparative Example 3 | 72 | 5 (Break at maximum stress) |
| Comparative Example 4 | 79 | 4 (Break at maximum stress) |

TABLE 2-continued

| | Bending strength (maximum stress) (MPa) | Elongation (at maximum stress) (%) |
|---|---|---|
| Comparative Example 5 | 76 | 4 (Break at maximum stress) |
| Comparative Example 6 | 100 | 6 (Break at maximum stress) |
| Comparative Example 7 | 84 | 6 (Break at maximum stress) |

As described above, nanosized, metal oxide-based fine particles can be obtained easily and efficiently from the organic silicon compounds according to the present invention.

Further, as is clear from the results in Table 1 and Table 2, it is seen that when the metal oxide-based fine particles obtained from the organic silicon compounds according to the present invention are added to resins, the bending strength and the elongation are significantly improved, and a high effect of improving toughness is obtained, compared with the resins to which no metal oxide-based fine particles are added, the resin composition containing silica fine particles according to the above-described related art, and the resin compositions containing fine particles fabricated with silicon compounds not having an essential constituent of the present organic silicon compounds.

Having thus described the present invention with reference to the exemplary embodiments, the present invention is not limited to the above-described exemplary embodiments. Various modifications understandable to those skilled in the art may be made to the constitution and details of the present invention within the scope thereof.

This application is based upon and claims the benefit of priority from Japanese Patent Application No. 2008-129585 filed May 16, 2008 and Japanese Patent Application No. 2009-26361 filed Feb. 6, 2009, the disclosure of which is incorporated herein in its entirety by reference.

The invention claimed is:

1. A metal oxide-based fine particle comprising:
a metal oxide-based core region;
an intermediate region comprising an alkoxyorganosiloxane condensate structure, the intermediate region being formed on the outer periphery of the core region; and
a surface region comprising an organic molecular chain or an organic silicon molecular chain or a reactive functional group,
wherein the metal oxide-based fine particle is a fine particle formed by a reaction between organometallic compounds each comprising a first section comprising a metal alkoxide group comprising a plurality of alkoxy groups each having 1 to 3 carbon atoms, a second section comprising an alkoxyorganosiloxane structure portion, the second section being bonded to the first section, and a third section comprising an organic molecular chain or an organic silicon molecular chain or a reactive functional group, the third section being bonded to the second section;
the metal oxide-based core region is a region formed by condensation between the metal alkoxide groups of the first sections;
the intermediate region is a region formed by condensation between the alkoxyorganosiloxane structure portions of the second sections; and
the surface region is a region comprising the organic molecular chains or the organic silicon molecular chains or the reactive functional groups of the third sections.

2. The metal oxide-based fine particle according to claim 1, wherein the first section is represented by formula (I):

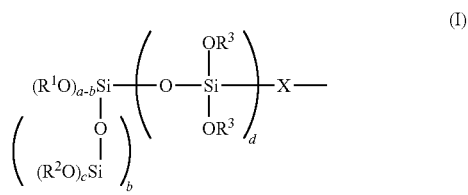

where $R^1$, $R^2$ and $R^3$ each independently represent an alkyl group having 1 to 3 carbon atoms, X represents a linking group, a represents 2 or 3, b represents 0, 1 or 2, c represents 2 or 3, and d represents 0 or a natural number, provided that a-b is 1 or more, one $R^1$ is directly bonded to a Si atom to which $R^1O$ is bonded when a is 2, and one $R^2$ is directly bonded to a Si atom to which $R^2O$ is bonded when c is 2;

the alkoxyorganosiloxane structure portion of the second section comprises a unit represented by formula (IIa):

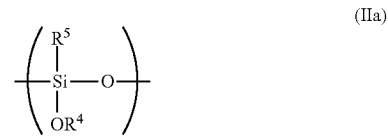

where $R^4$ represents an alkyl group having the number of carbon atoms equal to or more than the number of carbon atoms of $R^1$, $R^2$ and $R^3$, and $R^5$ represents an alkyl group having 1 to 10 carbon atoms, an aryl group having 6 to 10 carbon atoms, an alkenyl group having 2 to 10 carbon atoms, or an aralkyl group having 7 to 10 carbon atoms, and when there are a plurality of each of $R^4$ and $R^5$ in one molecule, $R^4$ and $R^5$ may each be the same as or different from each other; and the third section is represented by formula (III):

where $R^8$ represents an organic molecular chain or an organic silicon molecular chain or a reactive functional group, and Y represents a linking group.

3. The metal oxide-based fine particle according to claim 2, wherein $R^4$ is an alkyl group having one to four more carbon atoms than $R^1$, $R^2$ and $R^3$.

4. The metal oxide-based fine particle according to claim 2, wherein $R^1$, $R^2$ and $R^3$ are a methyl group or an ethyl group.

5. The metal oxide-based fine particle according to claim 2, wherein $R^1$, $R^2$ and $R^3$ are a methyl group or an ethyl group, and $R^4$ is an alkyl group having the same number of carbon atoms as $R^1$, $R^2$ and $R^3$.

6. The metal oxide-based fine particle according to claim 2, wherein d is 0.

7. The metal oxide-based fine particle according to claim 2, wherein the first section is represented by formula (IV):

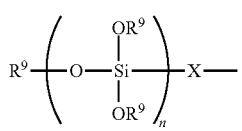  (IV)

where $R^9$ represents an alkyl group having 1 to 3 carbon atoms, X represents a linking group, and n represents an integer of 3 or more.

8. The metal oxide-based fine particle according to claim 7, wherein $R^4$ is an alkyl group having one to four more carbon atoms than $R^9$.

9. The metal oxide-based fine particle according to claim 2, wherein $R^5$ is an alkyl group.

10. The metal oxide-based fine particle according to claim 2, wherein the alkoxyorganosiloxane structure portion further comprising a unit represented by formula (IIb):

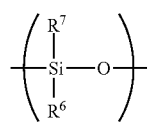  (IIb)

where $R^6$ and $R^7$ each independently represent an alkyl group having 1 to 10 carbon atoms, an aryl group having 6 to 10 carbon atoms, an alkenyl group having 2 to 10 carbon atoms, or an aralkyl group having 7 to 10 carbon atoms, and when there are a plurality of each of $R^6$ and $R^7$ in one molecule, $R^6$ and $R^7$ may each be the same as or different from each other; and a molar ratio of the unit represented by formula (IIa) and the unit represented by formula (IIb) ([IIa]/([IIa]+[IIb])) is in the range of 0.2 to 1.

11. The metal oxide-based fine particle according to claim 2, wherein the degree of polymerization of the alkoxyorganosiloxane structure portion of the second section is in the range of 2 to 30.

12. The metal oxide-based fine particle according to claim 2, wherein the degree of polymerization of the alkoxyorganosiloxane structure portion of the second section is in the range of 3 to 15.

13. A resin filler comprising the metal oxide-based fine particle as recited in claim 1.

14. A resin composition comprising the metal oxide-based fine particle as recited in claim 1 and a plastic.

15. A method for manufacturing a metal oxide-based fine particle comprising a metal oxide-based core region, an intermediate region comprising an alkoxyorganosiloxane condensate structure, the intermediate region being formed on the outer periphery of the core region, and a surface region comprising an organic molecular chain or an organic silicon molecular chain or a reactive functional group, the method comprising:

forming the metal oxide-based core region by a reaction between organometallic compounds each comprising a first section comprising a metal alkoxide group comprising a plurality of alkoxy groups each having 1 to 3 carbon atoms, a second section comprising an alkoxyorganosiloxane structure portion, the second section being bonded to the first section, and a third section comprising an organic molecular chain or an organic silicon molecular chain or a reactive functional group, the third section being bonded to the second section, to conduct condensation between the metal alkoxide groups of the first sections; and forming the intermediate region by the reaction to conduct condensation between the alkoxyorganosiloxane structure portions of the second sections, and forming the surface region comprising the organic molecular chains or the organic silicon molecular chains or the reactive functional groups located on the outer periphery of the intermediate region.

16. The method for manufacturing a metal oxide-based fine particle, according to claim 15, wherein the first section is represented by formula (I):

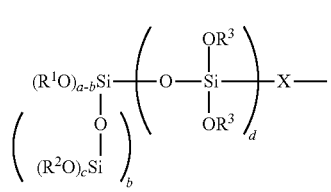  (I)

where $R^1$, $R^2$ and $R^3$ each independently represent an alkyl group having 1 to 3 carbon atoms, X represents a linking group, a represents 2 or 3, b represents 0, 1 or 2, c represents 2 or 3, and d represents 0 or a natural number, provided that a-b is 1 or more, one $R^1$ is directly bonded to a Si atom to which $R^1O$ is bonded when a is 2, and one $R^2$ is directly bonded to a Si atom to which $R^2O$ is bonded when c is 2;

the alkoxyorganosiloxane structure portion of the second section comprises a unit represented by formula (IIa):

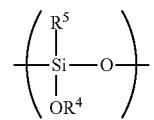  (IIa)

where $R^4$ represents an alkyl group having the number of carbon atoms equal to or more than the number of carbon atoms of $R^1$, $R^2$ and $R^3$, and $R^5$ represents an alkyl group having 1 to 10 carbon atoms, an aryl group having 6 to 10 carbon atoms, an alkenyl group having 2 to 10 carbon atoms, or an aralkyl group having 7 to 10 carbon atoms, and when there are a plurality of each of $R^4$ and $R^5$ in one molecule, $R^4$ and $R^5$ may each be the same as or different from each other; and the third section is represented by formula (III):

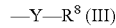

—Y—$R^8$ (III)

where $R^8$ represents an organic molecular chain or an organic silicon molecular chain or a reactive functional group, and Y represents a linking group.

17. The metal oxide-based fine particle according to claim 1, wherein the reaction speed of the alkoxy groups of the metal alkoxide group of the first section is higher than the reaction speed of the alkoxy groups of the second section in the organometallic compounds.

18. The method for manufacturing a metal oxide-based fine particle according to claim 15, wherein the reaction speed of the alkoxy groups of the metal alkoxide group of the first section is higher than the reaction speed of the alkoxy groups of the second section in the organometallic compounds.

* * * * *

UNITED STATES PATENT AND TRADEMARK OFFICE
CERTIFICATE OF CORRECTION

PATENT NO. : 8,507,095 B2
APPLICATION NO. : 12/991937
DATED : August 13, 2013
INVENTOR(S) : Masatoshi Iji, Naoki Morishita and Hiroyuki Kai It is certified that error appears in the above-identified patent and that said Letters Patent is hereby corrected as shown below:

In the Specification

Column 2, Line 1: Delete "niodulus," and insert -- modulus --

Column 6, Line 20: Delete "R3" and insert -- R5 --

Column 11, Line 9 (Approx.): Delete "R3" and insert -- R5 --

Column 12, Line 64: Delete "R3," and insert -- R5, --

Column 18, Line 16 (Approx.): Delete "s-caprolactone" and insert -- ε-caprolactone --

Column 23, Line 44-45: Delete "s-caprolactone" and insert -- ε-caprolactone --

Column 23, Line 49 (Approx.): Delete "s-caprolactone," and insert -- ε-caprolactone, --

Column 31, Line 59: Delete "10 g" and insert -- 10-3 g --

Column 35, Line 50: Delete "Example 2" and insert -- Example 2. --

Signed and Sealed this
Twenty-eighth Day of October, 2014

Michelle K. Lee
*Deputy Director of the United States Patent and Trademark Office*